(12) United States Patent
Tamura

(10) Patent No.: US 12,029,393 B2
(45) Date of Patent: Jul. 9, 2024

(54) ENDOSCOPE SYSTEM, CONTROL DEVICE, AND CONTROL METHOD OF CONTROL DEVICE

(71) Applicant: OLYMPUS CORPORATION, Tokyo (JP)

(72) Inventor: Kazuaki Tamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 77 days.

(21) Appl. No.: 17/973,772

(22) Filed: Oct. 26, 2022

(65) Prior Publication Data

US 2023/0050537 A1 Feb. 16, 2023

Related U.S. Application Data

(63) Continuation of application No. PCT/JP2020/018636, filed on May 8, 2020.

(51) Int. Cl.
*A61B 1/00* (2006.01)
*A61B 1/06* (2006.01)

(52) U.S. Cl.
CPC .......... *A61B 1/0655* (2022.02); *A61B 1/0638* (2013.01); *A61B 1/00009* (2013.01)

(58) Field of Classification Search
CPC ................................... A61B 1/00009
See application file for complete search history.

(56) References Cited

U.S. PATENT DOCUMENTS

| | | | |
|---|---|---|---|
| 2018/0247153 A1 | 8/2018 | Ganapati et al. | |
| 2020/0121175 A1 | 4/2020 | Morita | |
| 2020/0260940 A1 | 8/2020 | Kutsuma | |
| 2021/0012495 A1 | 1/2021 | Kamon et al. | |

FOREIGN PATENT DOCUMENTS

| | | |
|---|---|---|
| JP | 2017136405 A | 8/2017 |
| WO | 2017212946 A1 | 12/2017 |
| WO | 2018160288 A1 | 9/2018 |
| WO | 2018235178 A1 | 12/2018 |
| WO | 2019092948 A1 | 5/2019 |
| WO | 2019198637 A1 | 10/2019 |

OTHER PUBLICATIONS

International Search Report dated Jul. 14, 2020 issued in PCT/JP2020/018636.

*Primary Examiner* — Young Lee
(74) *Attorney, Agent, or Firm* — Scully, Scott, Murphy & Presser, P.C.

(57) ABSTRACT

An endoscope system includes a light source that emits illumination light, an image sensor that captures an image of an object toward which the illumination light is emitted, and a processor. The processor is configured to determine whether a fluid is present in the object. If the fluid is not present in the object, the processor switches to a first observation mode in which to illuminate the object by first illumination light. If the fluid is present in the object, the processor switches to a second observation mode in which to illuminate the object by second illumination light. The second illumination light includes is larger than the first illumination light in a relative ratio of long wavelength components.

19 Claims, 21 Drawing Sheets

| LEARNING IMAGE | IMAGING-TIME R: A: G: V: B | RECOMMENDED R: A: G: V: B |
|---|---|---|
| TIM1 | a1:b1:c1:d1:e1 | $\alpha 1 : \beta 1 : \gamma 1 : \delta 1 : \varepsilon 1$ |
| TIM2 | a2:b2:c2:d2:e2 | $\alpha 2 : \beta 2 : \gamma 2 : \delta 2 : \varepsilon 2$ |
| ⋮ | ⋮ | ⋮ |
| TIMn | an:bn:cn:dn:en | $\alpha n : \beta n : \gamma n : \delta n : \varepsilon n$ |

| LEARNING IMAGE | IMAGING-TIME R: A: G: V: B | FLUID | |
|---|---|---|---|
| | | DEGREE OF TRANS-PARENCY | BLOOD CONTENT |
| TIM1 | a1:b1:c1:d1:e1 | x1 | y1 |
| TIM2 | a2:b2:c2:d2:e2 | x2 | y2 |
| ⋮ | ⋮ | ⋮ | ⋮ |
| TIMn | an:bn:cn:dn:en | xn | yn |

| LEARNING IMAGE | RECOMMENDED R: A: G: V: B | BLEEDING POINT INFORMATION |
|---|---|---|
| TIM1 | $\alpha 1 : \beta 1 : \gamma 1 : \delta 1 : \varepsilon 1$ | SK1 |
| TIM2 | $\alpha 2 : \beta 2 : \gamma 2 : \delta 2 : \varepsilon 2$ | SK2 |
| ⋮ | ⋮ | ⋮ |
| TIMn | $\alpha n : \beta n : \gamma n : \delta n : \varepsilon n$ | SKn |

| LEARNING IMAGE | FLUID | | BLEEDING POINT INFORMATION |
| --- | --- | --- | --- |
| | DEGREE OF TRANS-PARENCY | BLOOD CONTENT | |
| TIM1 | x1 | y1 | SK1 |
| TIM2 | x2 | y2 | SK2 |
| ⋮ | ⋮ | ⋮ | ⋮ |
| TIMn | xn | yn | SKn |

LIGHT AMOUNT BALANCE

|  | NORMAL | UNDER-WATER 1 | UNDER-WATER 2 | UNDER-WATER 3 |
|---|---|---|---|---|
| LDV | V1 | V2 | V3 | V4 |
| LDB | B1 | B2 | B3 | B4 |
| LDG | G1 | G2 | G3 | G4 |
| LDR | R1 | R2 | R3 | R4 |
| COLOR TEMPERATURE | 6000k | 5500k | 5000k | 4500k |

BRIGHTNESS CORRECTION

|  | NORMAL | UNDER-WATER 1 | UNDER-WATER 2 | UNDER-WATER 3 |
|---|---|---|---|---|
| COEFFICIENT | ×1.0 | ×1.2 | ×1.4 | ×1.6 |

ENDOSCOPE SYSTEM, CONTROL DEVICE, AND CONTROL METHOD OF CONTROL DEVICE

CROSS REFERENCE TO RELATED APPLICATION

This application is a continuation of International Patent Application No. PCT/JP2020/018636, having an international filing date of May 8, 2020, which designated the United States, the entirety of which is incorporated herein by reference.

BACKGROUND

In performing a diagnosis or surgery using an endoscope, an object may be observed under water or through a fluid retained in an observation region. For example, in the case of using a bladder endoscope, a scope is inserted into a body cavity filled with a fluid to perform underwater observation. Otherwise, even in a use application or situation not based on underwater observation, an object may be observed through water fed from the endoscope or a body fluid. JP 2017-136405A discloses an endoscope device including an illumination section that has a plurality of kinds of light sources different in emission wavelength and a color tone control section that changes the ratio of light amounts emitted from the light sources to change the color tone of illumination light, thereby providing appropriate coloration to the object.

SUMMARY

In accordance with one of some aspect, there is provided an endoscope system comprising:
a light source that emits illumination light;
an image sensor that captures an image of an object toward which the illumination light is emitted; and
a processor,
the processor being configured to perform:
determining whether a fluid is present in the object;
in a case where the fluid is not present in the object, switching to a first observation mode in which to illuminate the object by first illumination light; and
in a case where the fluid is present in the object, switching to a second observation mode in which to illuminate the object by second illumination light, wherein
the second illumination light is larger than the first illumination light in a relative ratio of long wavelength components.

In accordance with one of some aspect, there is provided a control device comprising a processor,
the processor being configured to perform:
determining whether a fluid is present in the object;
in a case where the fluid is not present in the object, switching to a first observation mode in which to illuminate the object by first illumination light; and
in a case where the fluid is present in the object, switching to a second observation mode in which to illuminate the object by second illumination light, wherein
the second illumination light is larger than the first illumination light in a relative ratio of long wavelength components.

In accordance with one of some aspect, there is provided a control method of a control device, comprising:
determining whether a fluid is present in the object;
in a case where the fluid is not present in the object, switching to a first observation mode in which to illuminate the object by first illumination light; and
in a case where the fluid is present in the object, switching to a second observation mode in which to illuminate the object by second illumination light, wherein
the second illumination light is larger than the first illumination light in a relative ratio of long wavelength components.

DESCRIPTION OF EXEMPLARY EMBODIMENTS

Figure 1:
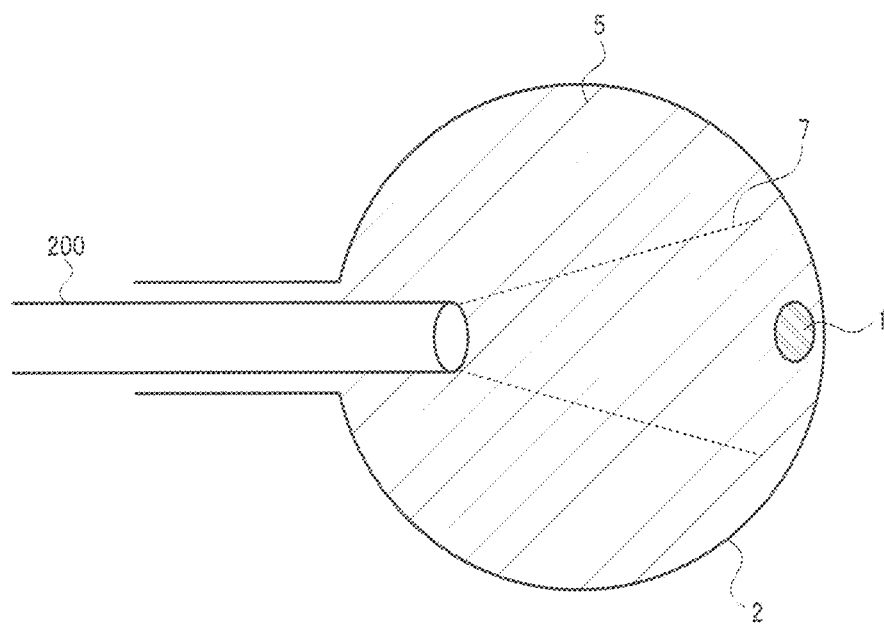
FIG. 1 illustrates an example of observation using an endoscope system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. First Configuration Example of Endoscope System

FIG. 1 illustrates an example of observation using an endoscope system in the present embodiment. The following description is based on a case where a body cavity is filled with a fluid as an example. However, the endoscope system in the present embodiment is also applicable to a case where a fluid is present between the leading end of the scope and the object, that is, a case where illumination light is applied to the object through the fluid and the object is observed through the fluid.

As illustrated in FIG. 1, a body cavity 2 such as a bladder or a joint is filled with a fluid 5. The fluid 5 is water, body fluid, or a combination thereof, for example. The fluid 5 may contain tissue fragments separated from the body cavity 2. A scope 200 of the endoscope system is inserted into the body cavity 2. The scope 200 irradiates an object 1 with illumination light 7 from its leading end through the fluid 5. The light returned from the object 1 reaches the scope 200 through the fluid 5, and the scope 200 captures an image of the object 1. The object 1 is an object in the body cavity 2 to be observed by the user, which is a lesion or the like, for example. However, the object 1 is not limited to a lesion or the like, and the region in the body cavity 2 seen in the field of view of the scope 200 is defined as the object 1.

In such underwater observation, there is an issue of reduction in the visibility of the object 1 under the influence of spectral characteristics and scattering characteristics of the fluid 5. There is also an issue of variation in the visibility of the object 1 depending on the kind of the fluid 5, the mixture concentration of the body fluid, the kind of tissue fragments, the content of tissue fragments, or a combination thereof. For example, if the fluid 5 is almost pure water, the observation image is affected by the spectral characteristics and scattering characteristics of the water. Otherwise, if the fluid 5 contains blood, the illumination light becomes unlikely to reach the object 1 due to the light absorption characteristics of hemoglobin and the field of view is reddish to reduce the visibility of the object 1. The degree of reduction in the visibility varies depending on the concentration of blood mixed in the fluid 5. Otherwise, if separated mucosal cells or bone fragments are floating in the fluid 5, the illumination light is scattered by the floating mucosal cells or the like, so that the illumination light becomes unlikely to reach the object 1 and the contrast of the observation image becomes lowered to reduce the visibility of the object 1. The degree of reduction in the visibility varies depending on the sizes and concentration of mucosal cells or the like mixed in the fluid 5. In the present embodiment, the illumination light 7 for observing the object 1 is regulated to suppress the reduction in the visibility caused by the fluid 5 as described above. There has not been conventionally disclosed any method for regulating illumination for observation to adjust an observation image for easy viewing. For example, JP 2017-136405A does not disclose a configuration in which the illumination mode is changed in correspondence with the turbid state of water supplied to the object.

Figure 2:
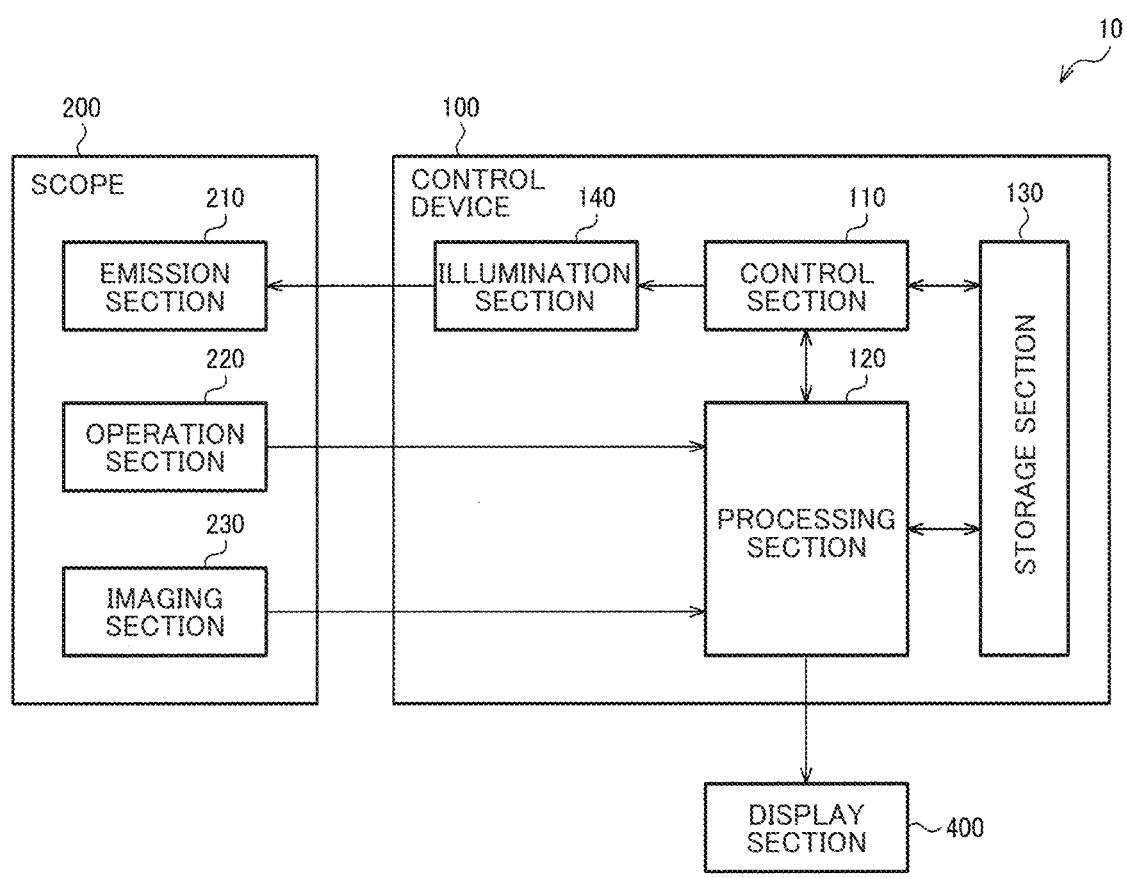
FIG. 2 illustrates a first configuration example of the endoscope system.

FIG. 2 illustrates a first configuration example of the endoscope system 10 in the present embodiment. The endoscope system 10 includes a control device 100, the scope 200, and a display section 400. Possible examples of the endoscope system 10 include an endoscope system for urinary organs such as a bladder endoscope or resectoscope, or a joint scope used in surgery or observation of joints. However, the endoscope system 10 may be either a rigid scope or a flexible scope, and may be an endoscope system used for various use applications and body parts, such as a surgical endoscope or an internal organ observation endoscope, for example.

The scope 200 is a part that is inserted into the body cavity 2 to illuminate the inside of the body cavity 2 and capture an image of the inside of the body cavity 2. The scope 200 includes an emission section 210, an operation section 220, and an imaging section 230. The scope 200 may further include a treatment tool such as an electrosurgical knife or forceps.

The emission section 210 is a device that emits illumination light from the leading end of the scope 200 to the object 1. The emission section 210 includes, for example, a light guide that guides the light from an illumination section 140 provided in the control device 100 and a lens that emits the light guided by the light guide to the object 1. The illumination section 140 may be provided separately from the control device 100.

The operation section 220 is a device for the user to operate the endoscope system 10. The operation section 220 includes buttons, switches, or dials, for example. In the present embodiment, the operation section 220 includes a water feed button for controlling feed of water from a water feed outlet in the scope 200.

The imaging section 230 is a device that captures an image of the inside of the body cavity 2 and outputs an imaging signal obtained by the image capturing to the control device 100. The imaging section 230 includes an object lens and an image sensor that captures an image formed by the object lens, for example.

The control device 100 performs image processing based on the imaging signal and operation control of the endoscope system 10. The control device 100 includes a control section 110, a processing section 120, a storage section 130, and an illumination section 140. The control device 100 is a device in which a circuit board provided with the control section 110, the processing section 120, and the storage section 130, and the illumination section 140 are stored in a casing. Otherwise, the control device 100 may be implemented by a general-purpose information processing device such as a PC that executes software describing the operations of the control device 100. Otherwise, a part of the control device 100 may be implemented by an information processing device separate from the control device 100 or by a cloud system. For example, AI processing described later may be executed by an information processing device provided separately from the control device 100 or a cloud system to which the control device 100 is connected via a network.

The illumination section 140 is a light source device that generates illumination light and enters the illumination light to the light guide of the emission section 210. The illumination section 140 includes a plurality of light sources that is independently controllable in light amount and is different in the wavelength region of emitted light. The light sources are LEDs, laser diodes, light sources that apply light emitted from the laser diodes to a fluorescent body to generate fluorescent light, or a combination thereof, for example. Otherwise, the illumination section 140 may be implemented by a white light source such as a xenon lamp and a filter device that can switch among a plurality of optical filters to transmit light in a desired wavelength region. The plurality of optical filters is different in spectral characteristics of transmittance. Although FIG. 2 illustrates separately the emission section 210 that is a lens and a light guide and the illumination section 140 that is a light source device, the lens, the light guide, and the light source device may be collectively called illumination section.

The processing section 120 is a circuit or device that controls the components of the endoscope system 10 and performs image processing on the imaging signal from the imaging section 230. The processing section 120 outputs the processed image to the display section 400 to display the image on the display section 400. The display section 400 is a display device such as a liquid crystal monitor, for example. The processing section 120 outputs image information necessary for controlling the spectrum of the illumination light to the control section 110. The image information may be the captured image itself or may be image parameters extracted from the captured image. The image parameters include contrast value, colors, brightness, and the like, for example.

The control section 110 is a circuit or device that controls the spectrum of illumination light by controlling the illumination section 140 based on the image information from the processing section 120. If the illumination section 140 includes a plurality of light sources, the control section 110 controls the spectrum of the illumination light by generating control parameters for controlling the on/off states and light amounts of the light sources from the image information. Otherwise, if the illumination section 140 includes a white light source and a filter device, the control section 110 controls the spectrum of the illumination light by generating control parameters for switching among optical filters in the filter device.

The control section 110 may generate intermediate information indicating the state of the fluid 5 from the image information, and then generate the control parameters from the intermediate information. The intermediate information indicates the degree of transparency of the fluid 5, the kind of a body fluid contained in the fluid 5, the concentration of the body fluid contained in the fluid 5, the kind of tissue fragments contained in the fluid 5, the concentration of tissue fragments contained in the fluid 5, or a combination thereof, for example. The processing section 120 may generate the intermediate information from the captured image, and the control section 110 may generate the control parameters based on the intermediate information from the processing section 120.

Each of the processing section 120 and the control section 110 is implemented by one or more circuits or devices. Otherwise, the processing section 120 and the control section 110 may be formed by an integrated circuit or device. Hardware constituting the processing section 120 and the control section 110 may be a processor, an FPGA, an ASIC, or a circuit board on which a plurality of circuit elements is mounted, for example.

The storage section 130 stores various kinds of data or programs to be used in processing performed by the control section 110 and the processing section 120. The storage section 130 is a semiconductor memory such as a RAM or a ROM, a magnetic storage device such as a hard disk drive, or an optical storage device such as an optical disk drive, for example. Specifically, the storage section 130 stores data or programs to be used in determining the appropriate spectrum of the illumination light in accordance with the state of the fluid 5.

For example, the storage section 130 may store a trained model obtained by machine learning. In this case, the control section 110 infers the control parameters of the illumination light appropriate to the fluid 5 from the image information or the intermediate information, by processing using the trained model. In the case of using the intermediate information, the control section 110 may infer the control parameters from the image information by processing using the trained model.

Otherwise, the storage section 130 may store a database for generating the control parameters described above. The database describes the spectral characteristics and scattering characteristics of the fluid 5, for example. The control section 110 determines the control parameters or the intermediate information, using information on the contrast value, brightness, and colors of the captured image and the database, for example. Otherwise, the database may be a lookup table in which the information on the contrast value, brightness, and colors of the captured image and the control parameters or the intermediate information are associated with each other. The control section 110 refers to the lookup table to acquire the control parameters or the intermediate information corresponding to the information on the contrast value, brightness, and colors of the captured image.

Otherwise, the storage section 130 may store a database for determining the control parameters of illumination light from the intermediate information. The database is a lookup table in which the intermediate information such as the degree of transparency of the fluid 5 and the control parameters of appropriate illumination light are associated with each other. The control section 110 refers to the lookup table to acquire the control parameters of the light amounts of the light sources or the optical filters to be selected in correspondence with the intermediate information.

According to the foregoing embodiment, the endoscope system 10 includes the illumination section 140 that emits the illumination light 7 in which spectra are variable, the imaging section 230 that captures an image of the object 1 to which the illumination light 7 is emitted, and the control section 110. The control section 110 controls the illumination section 140 to emit the illumination light 7 in which the spectra differ in accordance with a determination of whether the fluid 5 is present in the object 1 or in accordance with the degree of transparency of the fluid 5.

According to this, even if the visibility of the object 1 is decreased due to the mixture of tissue or body fluid in the fluid, it is possible to observe the object 1 with the illumination light 7 of the appropriate spectra in accordance with a determination of whether the fluid 5 is present in the object 1 or in accordance with the degree of transparency of the fluid 5. The appropriate spectra refer to spectra with which the visibility of the object 1 through the fluid 5 is improved in comparison with the case of observing the object 1 without changing the spectrum of the illumination light 7.

Specifically, the captured image is an image changed in contrast, for example, under influence of the degree of transparency of the fluid 5. Accordingly, if the captured image is input to the control section 110, the control parameters are determined in accordance with the captured image, thereby to realize the spectrum control in accordance with the degree of transparency. Otherwise, if the degree of transparency of the fluid 5 is input as control information to the control section 110, the control section 110 determines the control parameters in accordance with the degree of transparency of the fluid 5, thereby to realize the spectrum control in accordance with the degree of transparency. Otherwise, the degree of transparency of the fluid 5 is determined by the kind or concentration of the body fluid or tissue fragments contained in the fluid 5. Accordingly, if the kind or concentration of the body fluid or tissue fragments contained in the fluid 5 is input as intermediate information to the control section 110, the control section 110 determines the control parameters in accordance with the intermediate information to realize the spectrum control in accordance with the degree of transparency.

The "determination of whether the fluid 5 is present in the object 1" here specifically refers to a determination of whether the fluid 5 is present between the leading end of the scope 200 and the object 1.

The "degree of transparency of the fluid 5" refers to the transmittance of the illumination light in the fluid 5 present between the leading end of the scope 200 and the object 1. The transmittance refers to the degree to which the light is transmitted through the fluid 5. The transmittance refers to the ratio of the amount of light returned from the object 1 to the amount of light emitted from the leading end of the scope 200, for example. Otherwise, considering that the image parameters such as the contrast value of the captured image varies due to a decrease in the transmittance, for example, the image parameters such as the contrast value may be used as the transmittance. Assuming that the transmitted light is determined by the attenuation of the light in the fluid 5, the attenuation ratio may be used as the inverse of the transmittance. This case also applies to "in accordance with the degree of transparency of the fluid 5".

In the present embodiment, the control section 110 controls switching among a plurality of observation modes including two or more of a first observation mode to be selected in a case where the fluid 5 is not present, a second observation mode to be selected in a case where the degree of transparency of the fluid 5 is relatively high, and a third observation mode to be selected in a case where the degree of transparency of the fluid 5 is relatively low. The control section 110 performs at least one control of a control of switching, in accordance with switching between the first observation mode and the second observation mode, the illumination light 7 between first illumination light relating to the first observation mode and second illumination light relating to the second observation mode, a control of switching, in accordance with switching between the second observation mode and the third observation mode, the illumination light 7 between the second illumination light relating to the second observation mode and third illumination light relating to the third observation mode, and a control of switching, in accordance with switching between the first observation mode and the third observation mode, the illumination light between the first illumination light relating to the first observation mode and the third illumination light relating to the third observation mode.

According to this, it is possible to switch to the illumination light of the appropriate spectra in accordance with the state of the fluid 5 by switching among the observation modes in accordance with the state of the fluid 5.

The first to third observation modes are modes different in the spectrum of the illumination light. That is, the first to third illumination lights are different in spectrum. Specifically, the second illumination light is light of a spectrum in which the degree of transparency of the fluid 5 is higher than that of the first illumination light. The third illumination light is light of a spectrum in which the degree of transparency of the fluid 5 is higher than that of the second illumination light. What spectrum of light increases the degree of transparency varies depending on the kind of body fluid or tissue fragments contained in the fluid 5. An example of variation will be described later.

The illumination light control is not limited to the foregoing one. The number of observation modes is not limited to three, and a larger number of observation modes and illumination lights corresponding to the observation modes may be set. For example, the spectrum of the illumination light may be controlled to gradually change in accordance with the degree of transparency by switching among the observation modes in multi-stages in accordance with the degree of transparency.

Examples of switching among the first to third observation modes will be described with reference to FIGS. 3 to 7.

Figure 3:
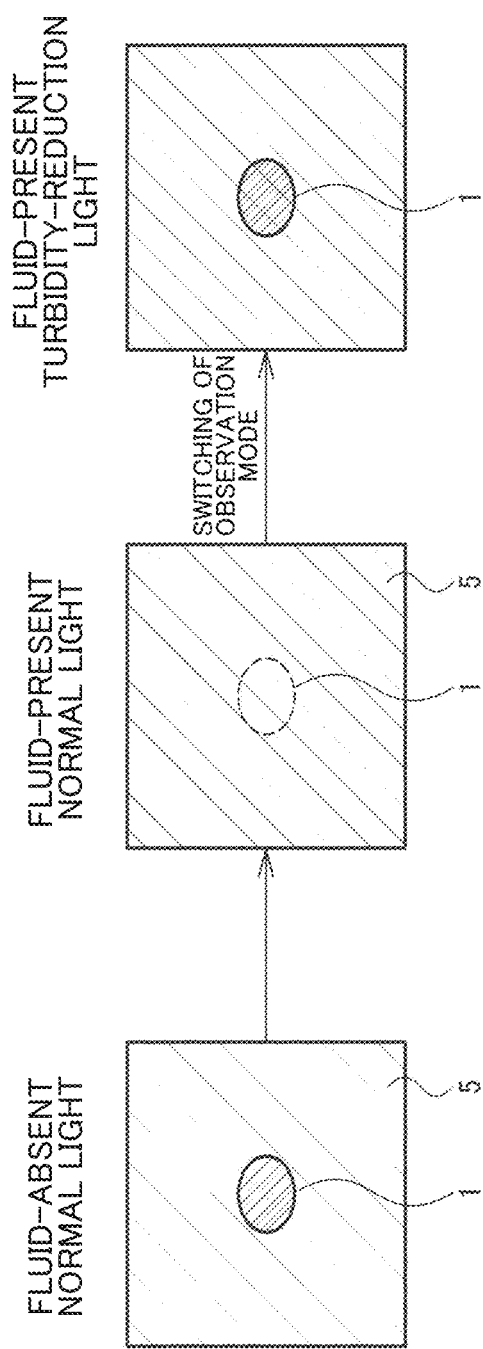
FIG. 3 illustrates an example of switching among observation modes in accordance with whether a fluid is present.

FIG. 3 illustrates an example of switching among observation modes in accordance with a determination of whether the fluid 5 is present. When the fluid 5 is not present, the control section 110 controls the illumination section 140 to emit normal light. When the control section 110 determines that the fluid 5 is present, the control section 110 changes the observation mode and controls the illumination section 140 to emit turbidity-reduction light. In this example, the normal light corresponds to the first illumination light in the first observation mode, and the turbidity-reduction light corresponds to the second illumination light or the third illumination light in the second observation mode.

The second illumination light is illumination light in which the relative ratio of long wavelength components in the spectrum is higher than that in the first illumination light. The third illumination light is illumination light in which the relative ratio of long wavelength components in the spectrum is higher than that in the second illumination light. In the case of shifting from the state without the fluid 5 to the state with the fluid 5, when the turbidity of the fluid 5 is relatively low, the illumination light is switched from the first illumination light to the second illumination light, and when the turbidity of the fluid 5 is relatively high, the illumination light is switched from the first illumination light to the third illumination light.

According to this, in the case of illuminating and imaging the object 1 through the fluid 5, it is possible to emit the illumination light with increased long wavelength components. If the fluid 5 has great light scattering like when the fluid 5 is turbid due to tissue fragments or the like, the long wavelength components causes less light scatting in the fluid 5 than the short wavelength components. Accordingly, using the illumination light with increased long wavelength components improves the visibility of the object 1 in the presence of the fluid 5.

The long wavelength components here refer to components in the long wavelength region of the illumination light. Specifically, the long wavelength components are components in the long wavelength region with respect to the middle of the wavelength region of the illumination light. Otherwise, if the wavelength region of the illumination light is divided into a plurality of color regions, the long wavelength components are components in a color region belonging to the long wavelength side with respect to the middle. For example, if the illumination light is visible light and the wavelength region of the visible light is divided into color regions of RGB, the long wavelength components are components in the R color region or components in the wavelength region belonging to the R color region.

Figure 4:
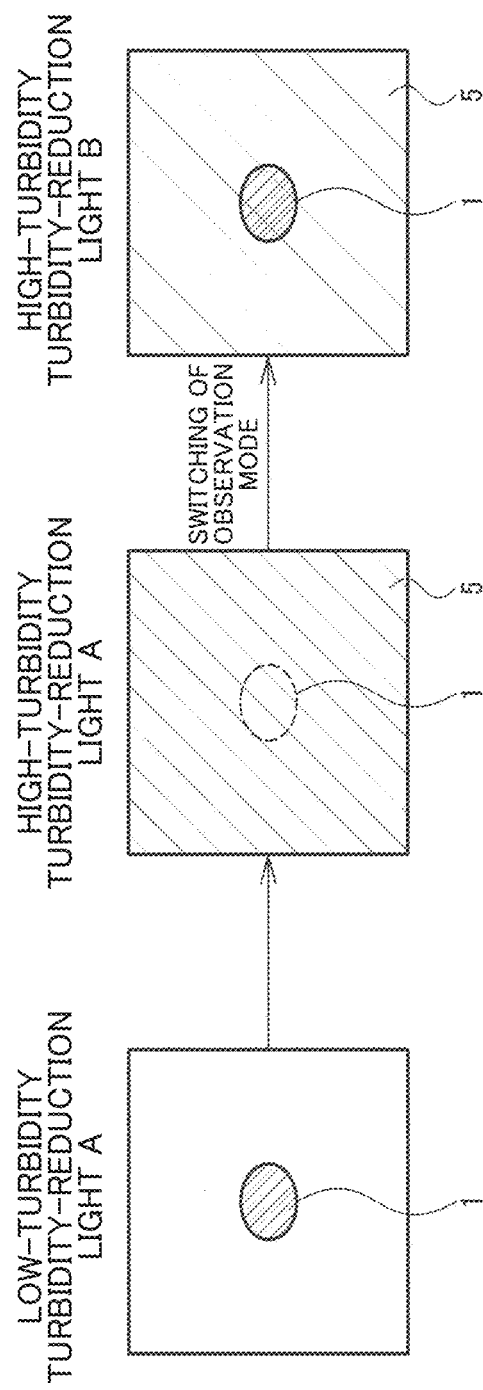
FIG. 4 illustrates an example of switching among observation modes in accordance with the degree of transparency of the fluid.

FIG. 4 illustrates an example of switching among observation modes in accordance with the degree of transparency of the fluid 5. If the turbidity of the fluid 5 is low, that is, if the degree of transparency of the fluid 5 is relatively high, the control section 110 controls the illumination section 140 to emit turbidity-reduction light A. If the control section 110 determines that the turbidity of the fluid 5 becomes high and the degree of transparency becomes low, the control section 110 changes the observation mode and controls the illumination section 140 to emit turbidity-reduction light B. In this example, the turbidity-reduction light A corresponds to the second illumination light in the second observation mode, and the turbidity-reduction light B corresponds to the third illumination light in the third observation mode.

If the fluid 5 has great light scattering like when the fluid 5 is turbid due to tissue fragments or the like, as the turbidity is higher, that is, as the degree of transparency is lower, the scattering becomes greater. According to the present embodiment, if the turbidity of the fluid 5 is high and the degree of transparency is low, the visibility of the object 1 can be improved by using the illumination light with increased long wavelength components.

In the present embodiment, the second illumination light and the third illumination light are illumination lights obtained by increasing the long wavelength components of the normal light. The degree of increase in the long wavelength components in the third illumination light is greater than the degree of increase in the long wavelength components in the second illumination light.

Figure 5:
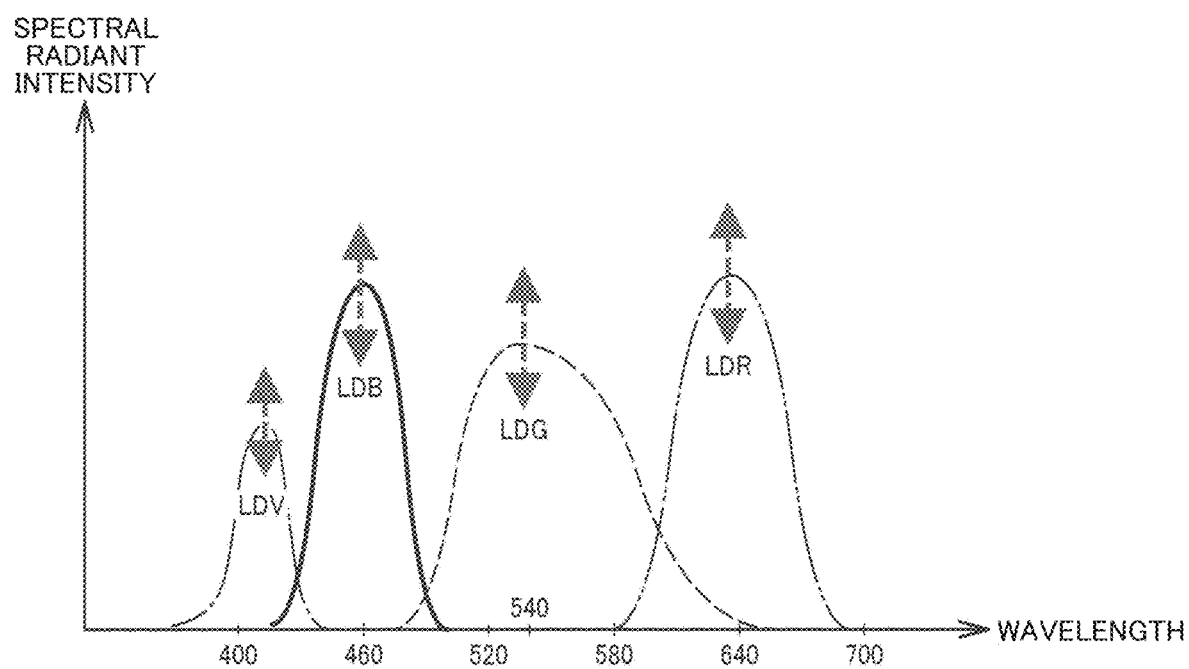
FIG. 5 illustrates an example of control for increasing long wavelength components of normal light.

FIG. 5 illustrates an example of control for increasing the long wavelength components of the normal light. In this example, the illumination section 140 includes a light source LDV that emits violet light, a light source LDB that emits blue light, a light source LDG that emits green light, and a light source LDR that emits red light. The ratio of light amounts of the light sources LDV, LDB, LDG, and LDR is defined as V:B:G:R, which is normalized. The control section 110 changes the spectra of the illumination light by switching among the light amount ratios V:B:G:R through the control parameters indicating the light amount ratios V:B:G:R. If the light amount ratio of the first illumination light is defined as $V:B:G:R=v1:b1:g1:r1$, the light amount ratio of the second illumination light is defined as $V:B:G:R=v2:b2:g2:r2$, and the light amount ratio of the third illumination light is defined as $V:B:G:R=v3:b3:g3:r3$, the relationship $r1<r2<r3$ holds.

According to this, in underwater observation, the illumination light adjusted in the long wavelength components with reference to the spectrum of the normal light is used. Accordingly, it is possible to perform underwater observation in a color tone similar to that in normal observation with the normal light.

The normal observation corresponds to an observation mode in which to observe the object assumed in the endoscope system, and for example, an observation mode in which to observe the object with white illumination light in the absence of fluid in the object. The normal light is illumination light in the normal observation mode, which corresponds to white illumination light, for example.

In the present embodiment, if the control section 110 controls the illumination section 140 such that the relative ratio of the long wavelength components in the spectrum of the illumination light becomes large, the processing section 120 performs image processing on the captured image so as to reduce the contribution of the long wavelength components. In the examples of FIGS. 3 and 4, the processing section 120 performs the image processing in the second observation mode and the third observation mode.

When the long wavelength components of the illumination light are increased, the image becomes increasingly reddish, or the color temperature of the image decreases. The influence of the long wavelength components of the illumination light on the image refers to "contribution of the long wavelength components". According to the present embodiment, since the image processing for reducing the contribution of the long wavelength components is performed, it is possible to reduce the reddishness of the image or suppress reduction in the color temperature of the image. This makes it possible to perform underwater observation in a color tone closer to the color tone for the observation with the normal light.

The image processing for reducing the contribution of the long wavelength components is color conversion processing on the captured image. The color conversion processing includes white balance processing by which to raise the color temperature of the image, or processing for reducing the components in the color region of the image corresponding to the long wavelength components of the illumination light. In the latter processing, for example, when the amount of light from the light source LDR is multiplied by x, the R components of the image are multiplied by 1/x.

In the present embodiment, the processing section 120 performs a structure enhancement process on the captured image such that the contrast of the region of interest becomes equal to or greater than a predetermined threshold.

According to this, even if the contrast of the region of interest decreases due to the body fluid or tissue fragments contained in the fluid 5, the contrast of the region of interest can be enhanced to be equal to or greater than the predetermined threshold by the structure enhancement process. This improves the visibility of the region of interest in underwater observation.

The region of interest may be the entire field of view of the imaging section 230 or a portion of the field of view. For example, the processing section 120 may perform lesion detection by image recognition using machine learning or the like and set the detected lesion region as the region of interest. The structure enhancement process is a process of increasing the high-frequency components of the image or a contrast enhancement process by gradation conversion, for example.

Figure 6:
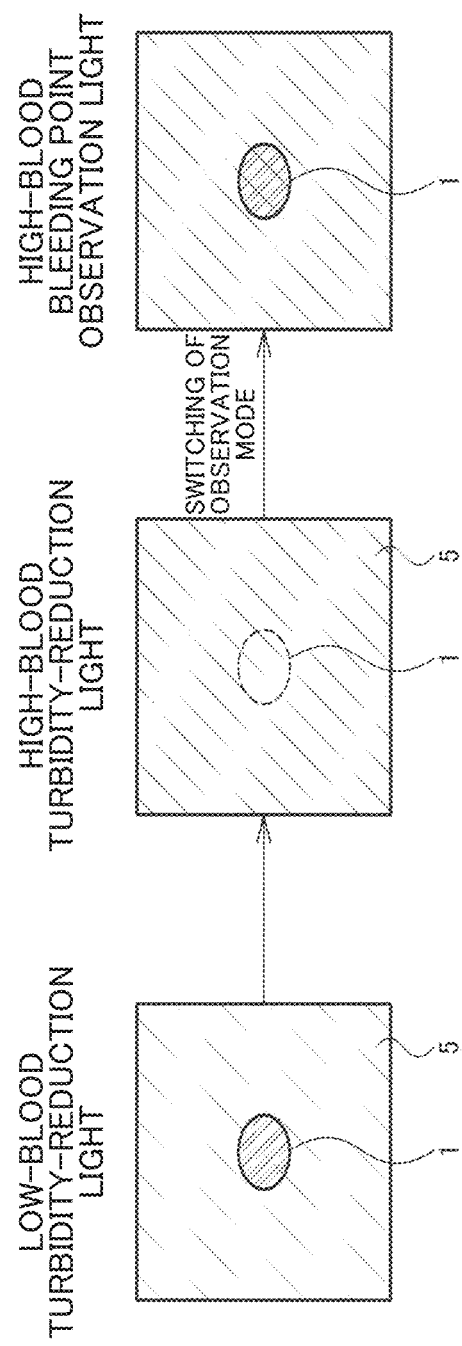
FIG. 6 illustrates an example of switching among observation modes in accordance with the amount of blood in the fluid.

FIG. 6 illustrates an example of switching among observation modes in accordance with the amount of blood in the fluid 5. When the blood contained in the fluid 5 is small in amount, that is, when the concentration of the blood is relatively low, the control section 110 controls the illumination section 140 to emit turbidity-reduction light. When the control section 110 determines that the blood contained in the fluid 5 increases in amount and the concentration of the blood becomes high, the control section 110 changes the observation mode and controls the illumination section 140 to emit bleeding point observation light. In this example, the turbidity-reduction light corresponds to the second illumination light in the second observation mode, and the bleeding point observation light corresponds to the third illumination light in the third observation mode.

During a surgical operation or the like using an endoscope, bleeding may occur due to incision or cut in the affected part. In underwater observation, the blood becomes mixed into the fluid 5 so that illumination and observation are performed through the blood-mixed fluid 5. Accordingly, the transmittance of the illumination light decreases due to absorption of hemoglobin, or the image becomes reddish due to the light absorption characteristics of hemoglobin, which leads to reduction in the visibility of the object 1. In the case of a large amount of bleeding with which the object 1 is hardly visible, it is desired to secure the field of view by arresting the bleeding. According to the present embodiment, if the amount of blood is small with which the object 1 is visible to some degree, the visibility can be improved by emitting the second illumination light that is turbidity-reduction light. If the amount of blood is large with which the object 1 is hardly visible, it is possible to improve the visibility of the bleeding point and assist the user in arresting the bleeding by emitting the third illumination light that is bleeding point observation light.

The second illumination light is illumination light in which the long wavelength components of the normal light are increased, and the third illumination light is special light that includes narrow band light corresponding to the long wavelength components. In this case as well, the third illumination light is larger than the second illumination light in the relative ratio of the long wavelength components in the spectrum.

According to this, if the degree of transparency of the fluid 5 is low and the visibility of the object 1 is very low, the special light can be emitted instead of the adjusted normal light. As a result, it is possible to emit the special light with a high degree of transparency to the body fluid or tissue fragments mixed in the fluid 5 or emit the special light allowing the specific object 1 to be easily seen, thereby to improve the visibility of the object 1.

The narrow band light here refers to light emitted by a light source such as a fluorescent lamp, a light emitting diode (LED) lamp, a laser light source, or a light source with a filter letting pass light in a certain wavelength, and the narrow band light has discrete spectral characteristics. The light with discrete spectral characteristics also includes light that has high intensity in a certain wavelength region and has significantly low intensity in the other wavelength region. The narrow band light may be light in a wavelength region narrower than the wavelength region of white illumination light. Otherwise, if the wavelength region of visible light is divided into RGB, the narrow band light may be light in a wavelength region narrower than the wavelength region of each of RGB.

Specifically, the object 1 is a biological body, and the fluid 5 contains blood. The third illumination light includes light in the wavelength region of amber. In the example of FIG. 6, the bleeding point observation light includes light in the wavelength region of amber. Depending on the use application, the second illumination light may include light in the wavelength region of amber, or the second illumination light and the third illumination light may include light in the wavelength region of amber. Hereinafter, the light in the wavelength region of ambler will also be called amber light.

Figure 7:
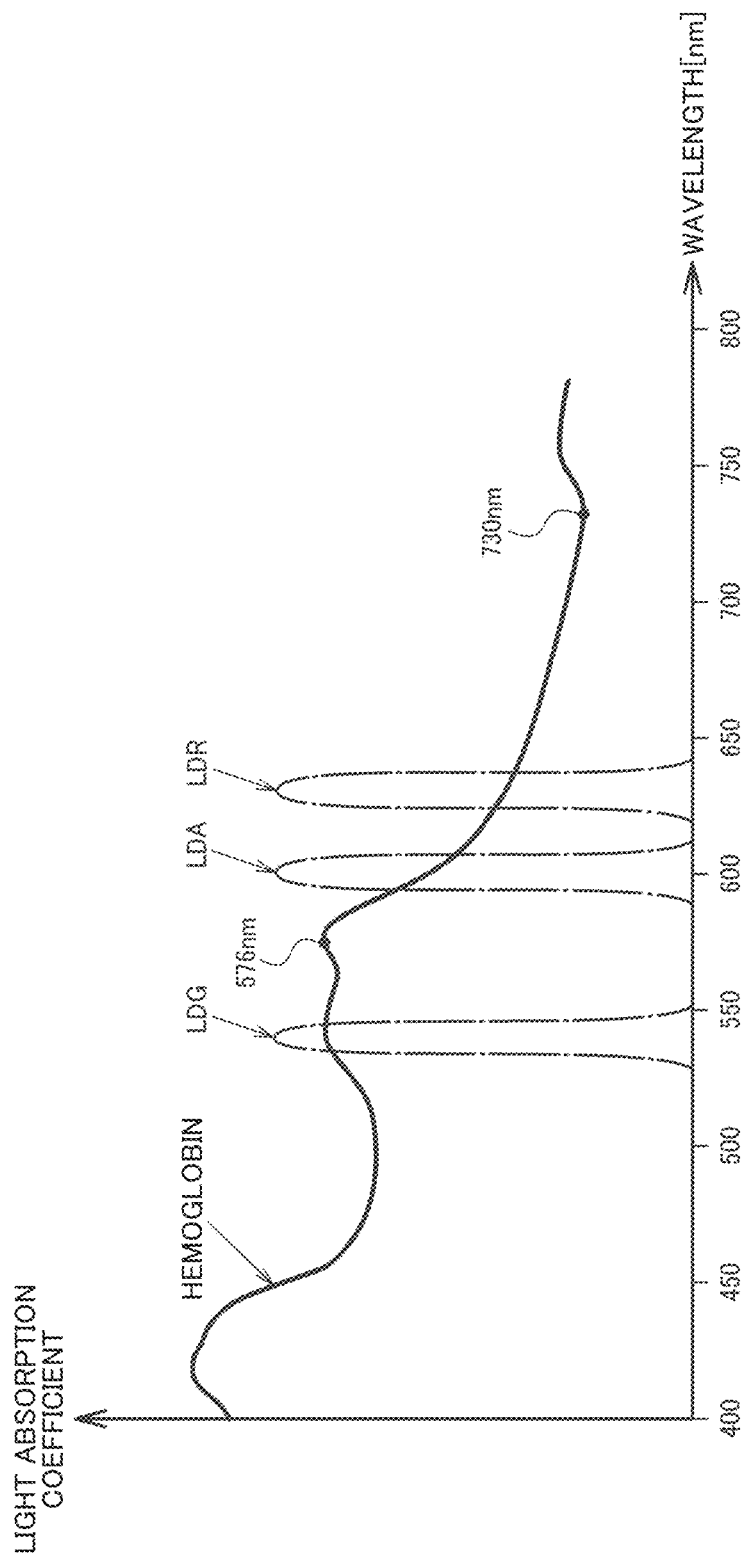
FIG. 7 illustrates an example of special light including amber light.

FIG. 7 illustrates an example of special light including amber light. The observation by the special light in FIG. 7 is also called red dichromatic imaging (RDI). The illumination section 140 includes the light sources LDV, LDB, LDG, and LDR described above, and a light source LDA emitting amber light. The control section 110 controls the illumination section 140 to emit light from the light sources LDG, LDA, and LDR.

The wavelength region of amber light emitted by the light source LDA is present between the wavelength region of green light emitted by the light source LDG and the wavelength region of red light emitted by the light source LDR. Specifically, the wavelength region of amber light is a wavelength region with a peak wavelength of 600 nm. The peak wavelength of amber light is not limited to 600 nm. Specifically, FIG. 7 illustrates the light absorption characteristics of venous blood as an example of light absorption characteristics of hemoglobin. In a range of 550 nm to 750 nm of the light absorption characteristics, the absorption coefficient exhibits the local maximum value at a point of wavelength of approximately 576 nm, and exhibits a local minimum value at a point of wavelength of approximately 730 nm. It is sufficient that the wavelength region of amber light is present between approximate 576 nm that is the local maximum value of the hemoglobin light absorption coefficient and approximate 730 nm that is the local minimum value of the hemoglobin light absorption coefficient. In the wavelength region of approximate 576 nm to approximate 730 nm, the shorter the wavelength of light, the greater the hemoglobin light absorption coefficient. That is, amber light is greater than red light in light absorption by hemoglobin.

Using the special light including amber light as used in RDI described above makes it easy to visually recognize the density of the blood in the fluid 5 so that the bleeding point with high density of blood can be visually recognized in an easy manner. The third illumination light has been described above as special light, but it is not limited to this. The third illumination light may be light in which amber light is added to the normal light.

In the present embodiment, the processing section 120 may perform a process of detecting the bleeding point in the object 1, based on the image captured when the object 1 is irradiated with the third illumination light including light in the wavelength region of amber, and perform a process of displaying the detected bleeding point.

According to this, if the visibility of the object 1 reduces due to a large amount of bleeding, it is possible to enhance the visibility of the bleeding point by emitting the third illumination light including light in the wavelength region of amber and to assist in arresting the bleeding by detecting and displaying the bleeding point.

The processing section 120 detects the bleeding point by a detecting process using machine learning as described later. Alternatively, the processing section 120 may detect the bleeding point using color information of the image, based on the fact that the vicinity of the bleeding point is higher in the intensity of red color than the surroundings.

In the foregoing description, the illumination light is changed in three steps as an example. Alternatively, the illumination light may be changed in more stages. Specifically, the control section 110 may control the illumination section 140 such that as the fluid 5 contains a larger amount of body fluid or more tissue fragments, the relative ratio of the long wavelength components in the spectrum of illumination light becomes higher.

According to this, it is possible to emit illumination light of appropriate spectrum in more stages in accordance with the concentration of body fluid or tissue fragments contained in the fluid 5, thereby improving the visibility of the object 1.

The endoscope system 10 also includes a supply section that supplies the fluid 5 to the object 1. The supply section is a water feed device 150 illustrated in FIG. 17, for example. The control section 110 may control the illumination section 140 such that as a larger amount of the fluid 5 is supplied by the supply section, the relative ratio of the long wavelength components in the spectrum of the illumination light becomes higher.

As a larger amount of the fluid 5 is supplied from the supply section, a larger amount of the fluid 5 is present in the body cavity. Thus, the amount of the fluid 5 between the leading end of the scope 200 and the object 1 becomes larger, that is, the distance of the leading end of the scope 200 and the object 1 becomes longer. Therefore, as a larger amount of the fluid 5 is supplied from the supply section, the degree of transparency decreases and the object 1 becomes harder to visually recognize. However, according to the present embodiment, it is possible to improve the visibility of the object 1 by increasing the ratio of the long wavelength components of the illumination light.

The control section 110 determines the supply amount of the fluid 5 based on a water feed control signal from the operation section 220 or water feed amount information from the supply section. For example, the water feed control signal is a signal that becomes active when water feeding is on, and the control section 110 determines the supply amount based on the active period of the water feed control signal. Otherwise, the water feed amount information is information that indicates the total amount of water feeding or the water feed amount per section time, and the control section 110 determines the supply amount based on the water feed amount information.

The control of the illumination light in accordance with the degree of transparency has been described above. This control may be performed in the following manner That is, if the degree of transparency of the fluid 5 is equal to or higher than a predetermined threshold, the control section 110 may control the illumination section 140 such that the difference between the image captured by the imaging section 230 and a reference image captured in the absence of the fluid 5 is equal to or smaller than a predetermined value. In addition, if the degree of transparency of the fluid 5 is lower than a predetermined threshold, the control section 110 may control the illumination section 140 such that the difference between the image captured by the imaging section 230 and a second reference image different from the reference image is equal to or smaller than a predetermined value.

According to this, if the degree of transparency of the fluid 5 is relatively high due to a small amount of body fluid or tissue fragments contained in the fluid 5, the obtained captured image is close to the reference image captured in the absence of the fluid 5. That is, the object can be observed even in underwater observation in a color tone similar to that in the normal observation, at a certain degree of transparency. If the degree of transparency of the fluid 5 is relatively low due to a large amount of body fluid or tissue fragments contained in the fluid 5, the obtained captured image is close to the second reference image different from the reference image. That is, the visibility of the object 1 can be prioritized with tolerance for a color tone different from that in the normal observation.

An example of a difference between the captured image and the reference image is a difference between the image parameters of the captured image and the image parameters of the reference image. The image parameters include the color phase, color balance, and brightness of the image, and a combination thereof, or statistical values thereof.

FIGS. 3 to 7 illustrate examples of enhancing the visibility by increasing the long wavelength components of the illumination light. However, the control of illumination light for enhancing the visibility is not limited to them. For example, the visibility may be enhanced by increasing the light in wavelength regions where light absorption is low in the spectral characteristics of the body fluid or tissue fragments contained in the fluid 5.

For example, in the case where the fluid 5 contains blood, the degree of transparency may be enhanced by using the light in wavelength regions where the light absorption coefficient of hemoglobin is low. That is, the ratio of blue components to violet components in the spectrum of the second illumination light may be higher than the ratio of blue components to violet components in the spectrum of the normal light. That is, assuming that the light amount ratio of the first illumination light that is the normal light is defined as V:B:G:R=v1:b1:g1:r1 and the light amount ratio of the second illumination light is defined as V:B:G:R=v2:b2:g2:r2, the relationship $b2/v2 > b1/v1$ holds. Depending on the use purpose, the ratio of blue components to violet components in the spectrum of the third illumination light may be higher than the ratio of blue components to violet components in the spectrum of the normal light, and the ratio of blue components to violet components in the spectra of the second illumination light and third illumination light may be higher than the ratio of blue components to violet components in the spectrum of the normal light.

As shown in FIG. 7, the light absorption characteristics of hemoglobin has a light absorption peak near a wavelength of 400 nm and near a wavelength of 520 nm, and the light absorption coefficients in between are relatively small. Since the wavelength region of the violet light is located around 400 nm and the wavelength region of the blue light is located between the two light absorption peaks described above, the blue light is less likely to be absorbed by hemoglobin than the violet light. Accordingly, emitting the third illumination light in which the ratio of the blue light is made higher than the normal light makes it possible to enhance the degree of transparency of the fluid 5 containing blood and improve the visibility of the object 1.

2. Example of Processing with Machine Learning

Next, a method for determining control parameters for controlling the spectrum of illumination light or detecting a bleeding point by processing with machine learning will be described. First, a learning device 500 that generates a trained model will be described.

Figure 8:
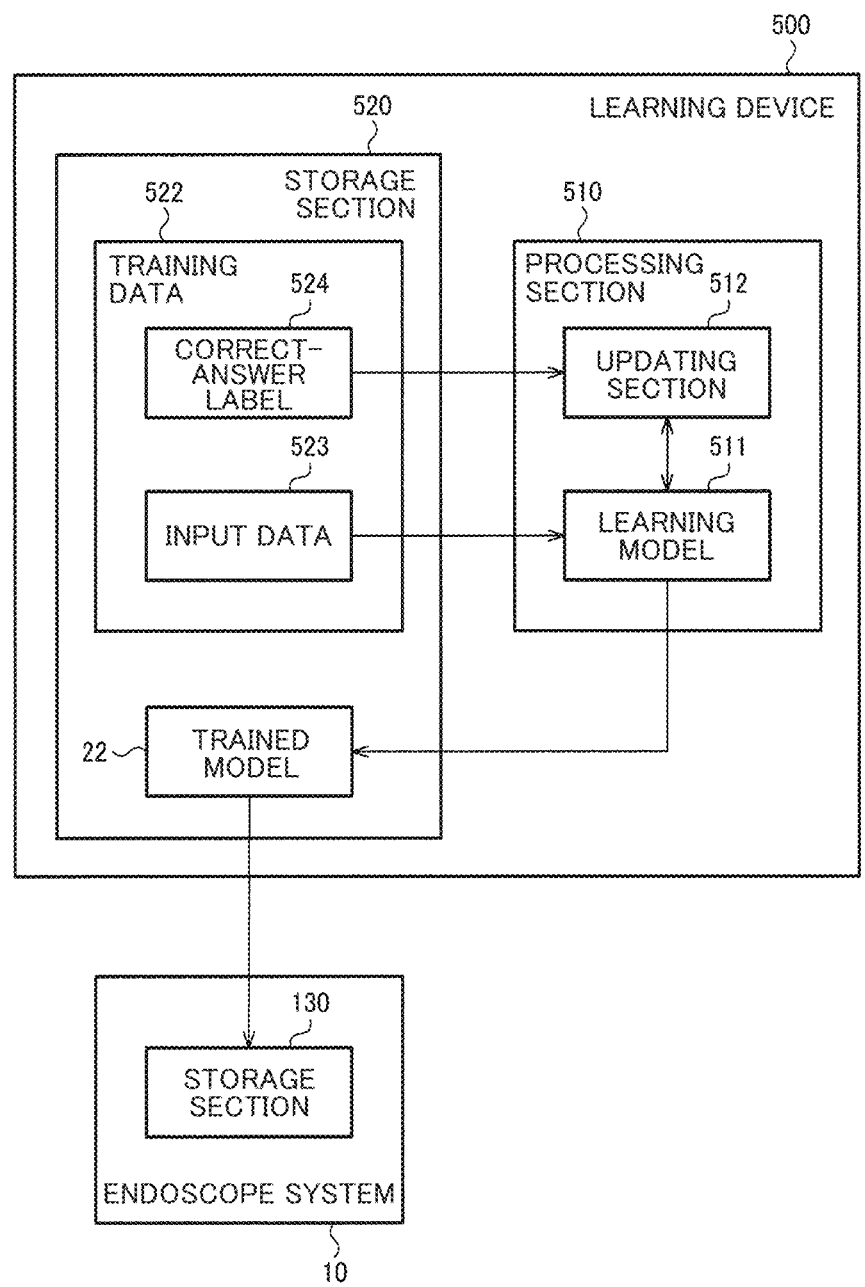
FIG. 8 illustrates a configuration example of a learning device.

FIG. 8 illustrates a configuration example of the learning device 500. The learning device 500 includes a storage section 520 and a processing section 510.

The storage section 520 is a semiconductor memory, a magnetic storage device, or an optical storage device. The storage section 520 stores training data 522 in which input data 523 and correct-answer labels 524 are associated with each other.

The processing section 510 is a processor, an FPGA, or an ASIC. The processing section 510 inputs the input data 523 to a learning model 511 to acquire inference results from the learning model 511. The processing section 510 includes an updating section 512. The updating section 512 updates the learning model 511 based on errors between the inference results and the correct-answer labels 524. This process is repeated to provide training. The processing section 510 stores a trained model 22 that is the learning model 511 having undergone the learning, in the storage section 520.

The trained model 22 is transferred to the endoscope system 10 and is stored in the storage section 130 of the endoscope system 10. The endoscope system 10 uses the trained model 22 stored in the storage section 130 to determine the control parameters.

If the inference in the endoscope system 10 is executed by general-purpose hardware such as a processor, the trained model 22 includes a program describing an inference algorithm and parameters for use in the inference algorithm. The parameters are obtained by learning. The inference algorithm is a neural network, for example, and in this case, the parameters are weight coefficients between nodes in the neural network. The inference process using the trained model 22 is implemented by the processing section 120 as general-purpose hardware executing the program using the parameters.

Otherwise, if the inference in the endoscope system 10 is executed by dedicated hardware obtained from the inference algorithm, the trained model 22 includes parameters for use in the inference algorithm. The inference process using the trained model 22 is implemented by the processing section 120 as dedicated hardware executing the inference algorithm using the parameters.

Next, examples of training data and examples of an inference process performed by a trained model having undergone machine learning with the training data will be described.

Figures 9, 10:
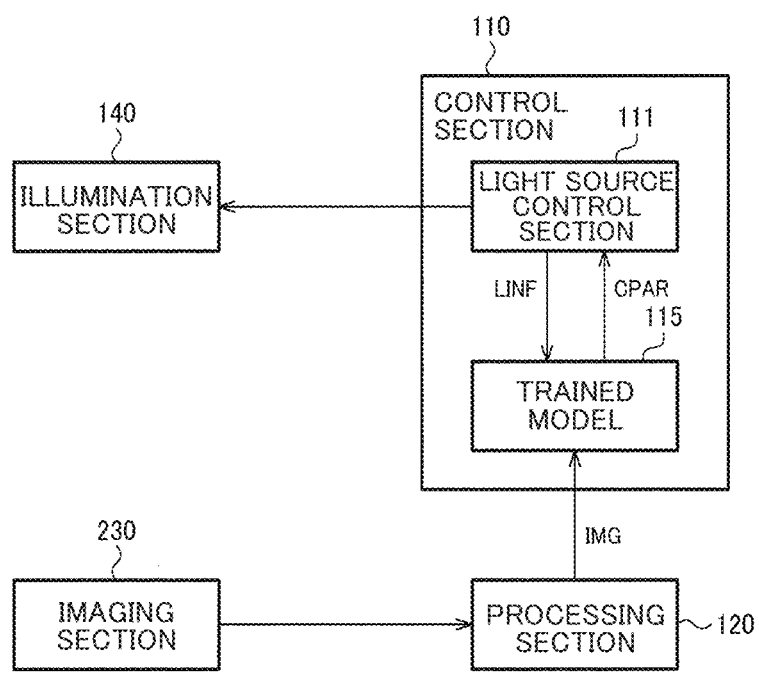
FIG. 9 illustrates a first example of training data.
FIG. 10 illustrates a configuration example of an endoscope system using a trained model having undergone learning with the first example of training data.

FIG. 9 illustrates a first example of training data. For each learning image TIMi, a light amount ratio at the time of image capturing R:A:G:B:V=ai:bi:ci:di:ei and a recommended light amount ratio R:A:G:B:V=αi:βi:γi:δi:εi are associated with each other, where i is an integer of 1 or larger to n or smaller, and n is an integer of 2 or larger. The learning images and the ratios of light amount at the time of image capturing constitute the input data 523, and the recommended light amount ratios constitute the correct-answer labels 524.

FIG. 10 illustrates a configuration example of an endoscope system using a trained model 115 having undergone learning with the first example of training data. In this example, only related constituent elements are illustrated in the drawing. The control section 110 inputs a captured image IMG from the processing section 120 and a control parameter LINF from a light source control section 111 to the trained model 115. The captured image IMG input to the trained model 115 may be a post-development color image or a pre-development original image such as a raw image. The captured image IMG is not limited to image data. For example, signal information on a pixel basis may be input to the trained model 115. The control parameter LINF indicate the light amount ratio R:A:G:B:V at the time of capturing of the captured image IMG. The control section 110 captures a control parameter CPAR by the inference process using the trained model 115. The control section 110 includes the light source control section 111, and the light source control section 111 controls the light amount ratios of the light sources of the illumination section 140 by the control parameter CPAR.

Figures 11, 12:
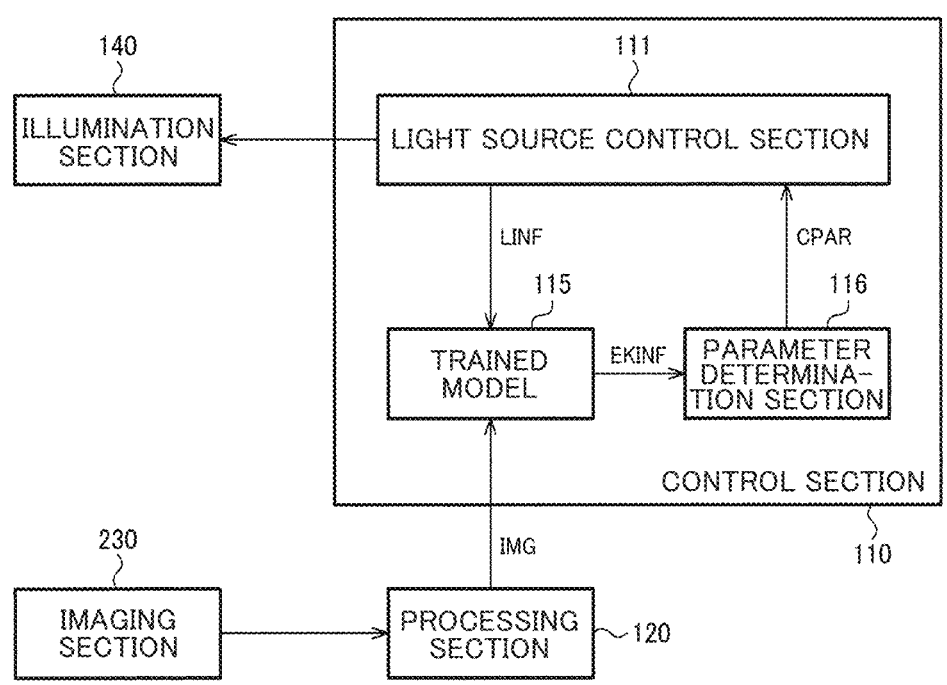
FIG. 11 illustrates a second example of training data.
FIG. 12 illustrates a configuration example of an endoscope system using a trained model having undergone learning with the second example of training data.

FIG. 11 illustrates a second example of training data. For each learning image TIMi, the light amount ratio at the time of image capturing R:A:G:B:V=ai:bi:ci:di:ei, a degree of transparency xi of the fluid, and a blood amount yi contained in the fluid are associated with one another. The learning images and the light amount ratios constitute the input data 523, and the degrees of transparency of the fluid and the amounts of blood contained in the fluid constitute the correct-answer labels 524.

FIG. 12 illustrates a configuration example of an endoscope system using a trained model 115 having undergone learning with the second example of training data. In this example, only related constituent elements are illustrated in the drawing. The control section 110 inputs the captured image IMG from the processing section 120 and the control parameter LINF from the light source control section 111 to the trained model 115. The control section 110 acquires information EKINF related to the fluid by an inference process using the trained model 115. The information EKINF indicates the degree of transparency of the fluid and the amount of blood contained in the fluid. Other information related to the fluid may be adopted as the training data, and the adopted information can be obtained by the inference process. The control section 110 includes a parameter determination section 116 and the light source control section 111. The parameter determination section 116 determines a control parameter CPAR from the information EKINF. For example, the parameter determination section 116 infers the control parameter based on a trained model acquired by machine learning of the relationship between the information related to the fluid and the control parameter. Alternatively, the parameter determination section 116 may determine the control parameter by referring to a lookup table in which the information related to the fluid and the control parameters are associated with each other. The light source control section 111 controls the light amount ratios of the light sources of the illumination section 140 by the control parameter CPAR from the parameter determination section 116.

In the examples of FIGS. 9 to 12, the control section 110 performs a process based on the trained model 115 acquired by machine learning of the relationship between the learning image and the information related to the fluid or the relationship between the learning image and the information related to recommended illumination light. The control section 110 determines the control parameter CPAR for controlling the spectrum of the illumination light based on the captured image IMG captured by the imaging section 230 and the trained model 115, and controls the illumination section 140 based on the determined control parameter CPAR. Specifically, the trained model 115 is a model acquired by machine learning of the relationship among the learning image, the information on the illumination light used in capturing the learning image, and the information related to the liquid. Alternatively, the trained model 115 is a model acquired by machine learning of the relationship among the learning image, the information on the illumination light used in capturing the learning image, and the information related to recommended illumination light.

According to this, it is possible to determine the spectrum of illumination light appropriate to the state of the fluid from the captured image, by the inference process using machine learning. By using machine learning, it is expected that the more optimized illumination light can be emitted in various states of the fluid.

Figures 13, 14:
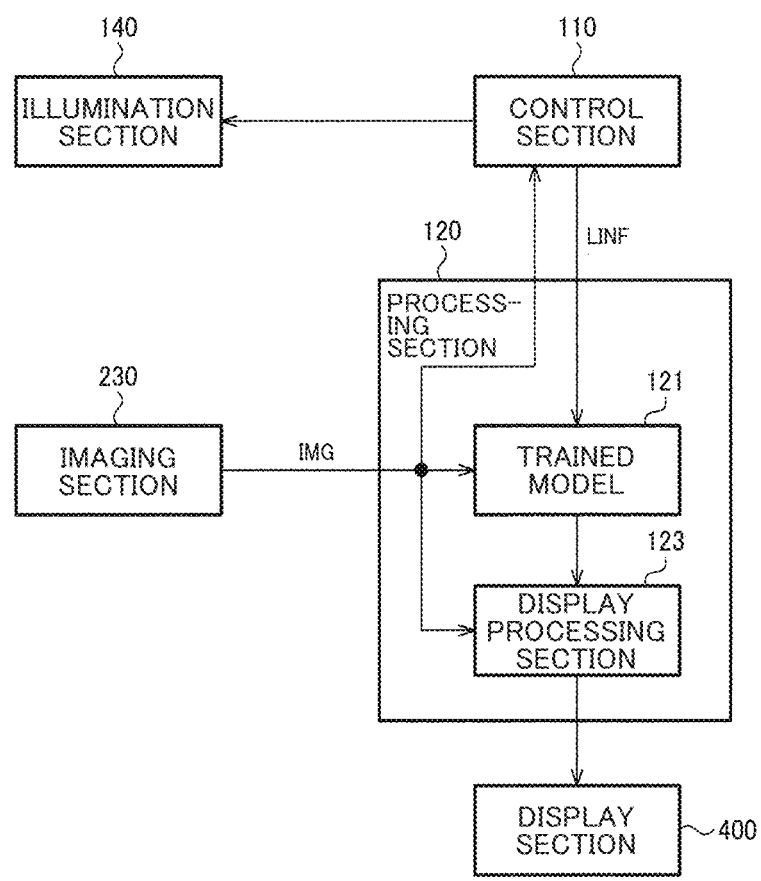
FIG. 13 illustrates a third example of training data.
FIG. 14 illustrates a configuration example of an endoscope system using a trained model having undergone learning with the third example of training data.

FIG. 13 illustrates a third example of training data. For each learning image TIMi, the light amount ratio at the time of image capturing R:A:G:B:V=ai:bi:ci:di:ei and bleeding point information SKi are associated with each other. The learning images and the light amount ratios at the time of image capturing constitute the input data 523, and the bleeding point information constitutes the correct-answer labels 524. The bleeding point information SKi is information indicating the position or region of a bleeding point in the image, which includes a rectangle containing the bleeding point or a line along the boundary of the bleeding point, for example.

FIG. 14 illustrates a configuration example of an endoscope system using a trained model 121 having undergone learning with the third example of training data. In this example, only related constituent elements are illustrated in the drawing. The processing section 120 inputs the captured image IMG and the control parameter LINF from the control section 110 to the trained model 121. The processing section 120 detects the position or region of the bleeding point by an inference process using the trained model 121. The processing section 120 includes a display processing section 123. The display processing section 123 displays the detected position or region of the bleeding point together with the captured image IMG on the display section 400. The control section 110 determines the control parameter CPAR in the manner described with reference to FIGS. 9 to 12.

Figures 15, 16:
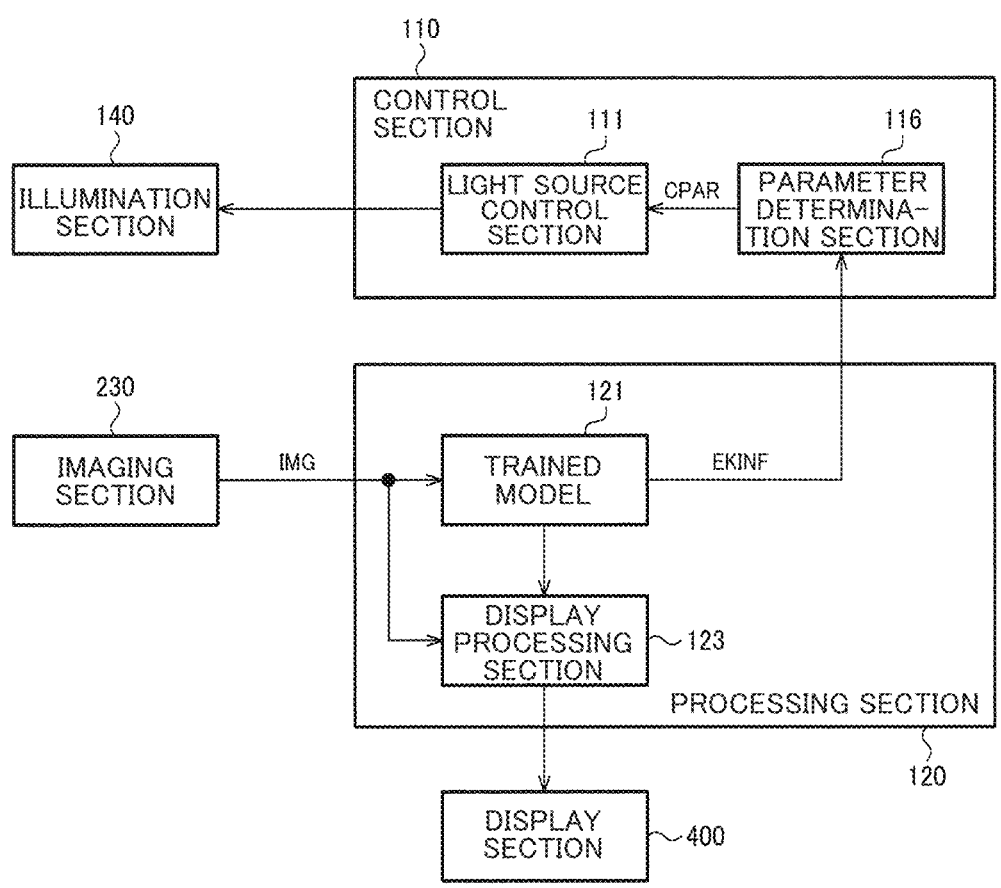
FIG. 15 illustrates a fourth example of training data.
FIG. 16 illustrates a configuration example of an endoscope system using a trained model having undergone learning with the fourth example of training data.

FIG. 15 illustrates a fourth example of training data. For each learning image TIMi, the degree of transparency xi of the fluid, the blood amount yi contained in the fluid, and the bleeding point information SKi are associated with one another. The learning images constitute the input data 523, and the degrees of transparency, the blood amounts, and the bleeding point information constitute the correct-answer labels 524.

FIG. 16 illustrates a configuration example of an endoscope system using the trained model 121 having undergone learning with the fourth example of training data. In this example, only related constituent elements are illustrated in the drawing. The processing section 120 inputs the captured image IMG to the trained model 121. The processing section 120 detects the information EKINF related to the fluid and the position or region of the bleeding point by an inference processing using the trained model 121. The information EKINF indicates the degree of transparency of the fluid and the amount of blood contained in the fluid. The processing section 120 contains the display processing section 123. The display processing section 123 displays the detected position or region of the bleeding point together with the captured image IMG on the display section 400. The control section 110 includes the parameter determination section 116 that determines the control parameter CPAR from the information EKINF. The light source control section 111 controls the light amount ratios of the light sources of the illumination section 140 by the control parameter CPAR from the parameter determination section 116.

In the examples of FIGS. 13 to 16, the processing section 120 performs a process based on the trained model 121 that is acquired by machine learning of the relationship between the learning image and the bleeding point in the object. The processing section 120 detects the bleeding point based on the captured image IMG captured by the imaging section 230 and the trained model 121. Specifically, the trained model 121 is a model that is acquired by machine learning of the relationship among the learning image, the information related to the fluid, and the bleeding point. Alternatively, the trained model 121 is a model that is acquired by machine learning of the relationship among the learning image, the information on illumination light used in capturing the learning image, and the bleeding point.

According to this, it is possible to detect the bleeding point from the captured image by an inference process using machine learning. By using machine learning, it is expected that more optimized bleeding point detection can be implemented in various states of the illumination light or fluid.

The trained model for determining the control parameters and the trained model for detecting the bleeding point may be integrated. In this case, in the training data, the learning images, the control parameters, and the bleeding point information are at least associated with one another. The learning images constitute the input data, and the control parameters and the bleeding point information constitute the correct-answer labels. The control section 110 inputs the captured image to the trained model, and acquires the control parameter and the bleeding point information by an inference process using the trained model. The inference process may be executed by the processing section 120.

The control section 110 and the processing section 120 in the present embodiment described above may be partially or entirely implemented by programs. In that case, the endoscope system 10 may be configured as described below.

That is, the endoscope system 10 includes a memory that stores information and a processor that operates based on the information stored in the memory. The information includes programs and various types of data, for example. The programs describe some or all of functions of the control section 110 and the processing section 120. The processor executes the programs to implement some or all of functions of the control section 110 and the processing section 120.

Specifically, the endoscope system 10 includes the illumination section 140, the imaging section 230, and the processor. The processor controls the illumination section 140 to emit illumination light in which the spectra differ in accordance with a determination of whether the fluid is present in the object or in accordance with the degree of transparency of the fluid. A part of the present embodiment is described here, but the processor can execute some or all of functions of the control section 110 and the processing section 120 described in relation to the present embodiment.

The processor includes hardware, and the hardware may include at least one of a circuit that processes digital signals and a circuit that processes analog signals. For example, the processor may be formed of one or more circuit devices mounted on a circuit board and one or more circuit elements. The one or more circuit devices are ICs or the like, for example. The one or more circuit elements are resistances, capacitors, or the like, for example. The processor may be a central processing section (CPU), for example. However, the processor is not limited to a CPU and may be any of various kinds of processors such as a graphics processing section (GPU) or a digital signal processor (DSP). The processor may be an integrated circuit device such as an application specific integrated circuit (ASIC) or a field programmable gate array (FPGA). The processor may include an amplifier circuit and a filter circuit that process analog signals. The memory may be a semiconductor memory such as an SRAM or a DRAM, a register, a magnetic storage device such as a hard disk device, or an optical storage device such as an optical disk device. For example, the memory stores computer-readable commands, and when the commands are executed by the processor, the functions of the components of the endoscope device are implemented as processes. The commands here may be commands in a command set constituting programs or commands for instructing the hardware circuit of the processor to perform operations.

The programs can be stored in an information storage medium that is a computer-readable medium, for example. The information storage medium can be implemented by an optical disk, a memory card, an HDD, or a semiconductor memory, for example. The semiconductor memory is a ROM, for example. The control section 110 and the processing section 120 perform various processes in the present embodiment, in accordance with the programs and data stored in the information storage medium.

The present embodiment described above may be executed as an illumination control method. The illumination control method can also be said to be an operating method of the endoscope system 10. Specifically, in the illumination control method, illumination light variable in spectrum is emitted, an object irradiated with the illumination light is imaged, and a control is performed to emit the illumination light in which spectra differ in accordance with a determination of whether a fluid is present in the object or in accordance with the degree of transparency of the fluid. A part of the present embodiment is described herein, but the operations of the endoscope system 10 described in relation to the present embodiment can be executed as the illumination control method.

3. Application Examples

Several examples of specific applications of the endoscope system 10 in the present embodiment will be described.

A first application example is a urinary organ scope such as a cystourethroscope or a resectoscope. The resectoscope is an endoscope that is used for prostatectomy. The following first scene and second scene are conceivable in the medical procedure using a urinary organ scope.

The first scene is an observation scene in which the fluid is turbid redly with blood. Employed in this scene is a technique using illumination light in a wavelength region in which the light absorbance of hemoglobin is low or a technique using illumination light increased in light amount in a wavelength region in which the light absorbance of hemoglobin is high. The following first spectrum example and second spectrum example are conceivable.

In the first spectrum example, with reference to white illumination light using red light, green light, blue light, and violet light, the light amount of the blue light is made larger than the light amount of the violet light, and the light amount of first green light is made larger than the light amount of second green light, thereby to enhance the visibility while maintaining whiteness. The second green light and the first green light both belong to the wavelength region of the green light, and the second green light is longer in wavelength than the first green light. The peak wavelength of the second green light is about 580 nm. In the light absorption characteristics of hemoglobin, light absorbance peaks are present in the wavelength regions of the violet light and the second green light. Thus, the light amounts in the wavelength regions are made relatively low to enhance the transmittance of the illumination light. In addition, since the wavelength of the blue light is longer than the wavelength of the violet light and the wavelength of the first green light is shorter than the wavelength of the second green light, the light amount control affects the color tone in the opposite direction so that it is easy to maintain whiteness.

In the second spectrum example, with reference to white illumination light, illumination light with an increased ratio of blue light is used to enhance the visibility. Considering that the visible light region of the illumination light is divided into blue, green, and red, hemoglobin is high in the absorbance of blue light and thus the blue components of the captured image decrease. In the second spectrum example, the ratio of the blue light is increased to compensate for the decrease in the blue components of the image.

The second scene is an observation scene in which the fluid is whitish due to relatively large tissue fragments. Employed in this scene is illumination light with increase in long wavelength components less vulnerable to the influence of scattering. Since the use of the red light alone results in an image with a low resolution of the surface structure, the blue light and the green light are also used for illumination light. In the spectrum example in the second scene, with reference to the white illumination light using the red light, the green light, the blue light, and the violet light, the light amount of the red light is made larger than the light amount of the violet light plus the light amount of the blue light.

The second application example is an arthroscope that is used for joint surgery. In a medical procedure using an arthroscope, an observation scene in which the fluid is whitish due to fine bone fragments is conceivable. In this scene, since the influence of scattering is larger than in the second scene using a urinary organ scope, illumination light with further increase in long wavelength components is used. That is, in this scene, the ratio of the light amount of the red light to the light amount of the violet light plus the light amount of the blue light is made higher than that in the second scene using a urinary organ scope.

4. Second Configuration Example

Figure 17:
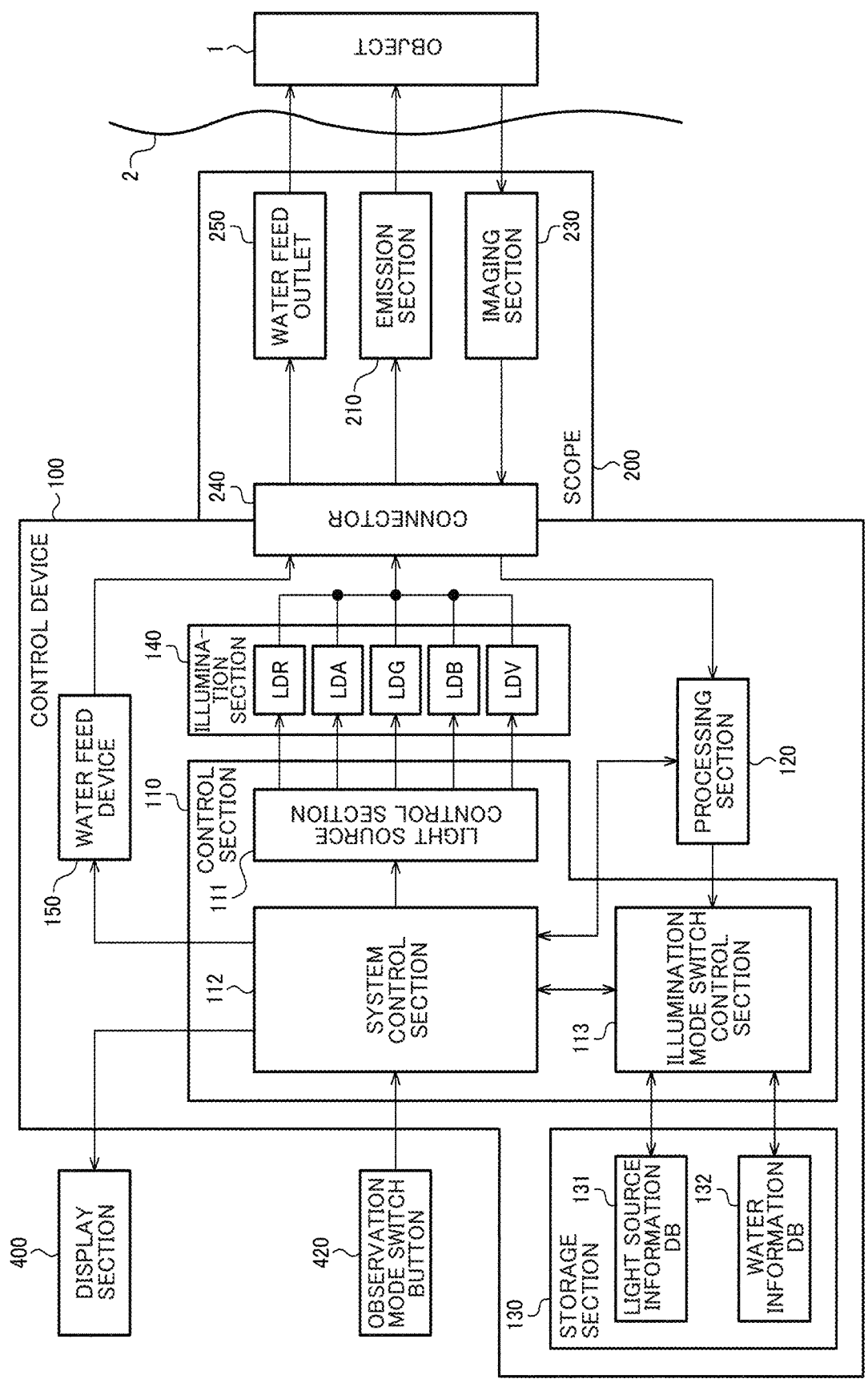
FIG. 17 illustrates a second configuration example of an endoscope system.

FIG. 17 illustrates a second configuration example of an endoscope system 10. The endoscope system 10 includes a control device 100, a scope 200, a display section 400, and an observation mode switch button 420. Constituent elements already described in relation to the first configuration example are given identical reference signs and description thereof will be omitted as appropriate.

The scope 200 includes an emission section 210, an imaging section 230, a water feed outlet 250, and a connector 240. The water feed outlet 250 is an opening provided at the leading end of the scope 200 to feed water to the object 1. The connector 240 is also provided in the control device 100, and the scope 200 and the control device 100 are connected together via the connectors 240 in the scope 200 and the connectors 240 in the control device 100.

The control device 100 includes a control section 110, a processing section 120, a storage section 130, and an illumination section 140. The control section 110 includes a light source control section 111, a system control section 112, and an illumination mode switch control section 113. The storage section 130 stores a light source information database 131 and a water information database 132. The illumination section 140 includes light sources LDR, LDA, LDG, LDB, and LDV. In the case of not using amber light, the light source LDA may be omitted.

The processing section 120 performs image processing on an imaging signal from the imaging section 230 to generate a captured image. The system control section 112 displays the captured image from the processing section 120 on the display section 400.

The system control section 112 switches the observation mode in response to an operation input to the observation mode switch button 420. The illumination mode switch control section 113 selects, in accordance with the switched observation mode, a predetermined light source control condition from a setting table included in the light source information database 131. The illumination mode switch control section 113 acquires image information based on the captured image from the processing section 120, and selects the light source control condition in accordance with the image information. The image information indicates the color and brightness of the image, or a combination thereof, for example. The system control section 112 outputs the selected light source control condition to the light source control section 111. The light source control section 111 outputs control parameters for controlling the light amounts of the light sources to the illumination section 140, based on the light source control condition. The light sources of the illumination section 140 emit the light by the amounts specified by the control parameters. The illumination light emitted from the illumination section 140 is applied to the object 1 from the emission section 210 of the scope 200.

The water feed device 150 feeds water from the water feed outlet 250 of the scope 200 to the object 1 in response to the instruction from the system control section 112. The water feed device 150 corresponds to the supply section described above in relation to the first configuration example.

The information included in the light source information database 131 will be described. The light source information database 131 has information on peak wavelengths and information on the relationship between drive current and optical output for the individual light sources installed in the endoscope system 10. The light source information database 131 also has output balance information for realizing white light by combination of lights from the light sources and total illumination amount information. The peak wavelengths and wavelength regions of the light sources and an example of white light are as illustrated in FIG. 5, for example. Although not illustrated in the drawings, the illumination section 140 may have photodiodes for monitoring the light amounts of the light sources. The light source control section 111 may control the light sources based on the outputs of the photodiodes and the light source control condition.

The light source information database 131 has light distribution characteristics of illumination light emitted from an illumination window and information on central brightness derived from the illumination light amount and distribution characteristics. The illumination window is a window that is provided at the leading end of the scope 200 and through which the illumination light is emitted. A portion of the illumination lens of the emission section 210 exposed at the leading end of the scope 200 illustrated in FIG. 17 corresponds to the illumination window. The light distribution characteristics may be held for emission light from each light source. The central brightness is also called central intensity. Assuming that the center line of the illumination window is at angle of zero degree, the light distribution characteristics indicate the relationship between the angle formed by the center line and the emission direction and the illumination intensity in the emission direction. For example, in the light distribution characteristics, the intensity is maximum at an angle of zero degree, and the larger the angle, the more the intensity is attenuated.

The light source information database 131 also has information related to the configuration of the illumination window based on ID information of the scope 200 connected to the control device 100. The information related to the configuration of the illumination window includes the number and arrangement of illumination window(s) provided at the leading end of the scope 200, the diameter of the illumination window(s), or a combination thereof, for example.

The information included in the water information database 132 will be described. The water information database 132 has information on the degree of transparency of the water fed from the water feed outlet 250 in the visible light region. The information on the degree of transparency includes a wavelength-absorption coefficient relationship, a wavelength-scattering coefficient relationship, or both, for example. The water information database 132 also has information on the refractive index of water as an optical characteristic of water material. The information on the refractive index is information on Fresnel reflection by water. The water information database 132 has a refractive index of 1.333, for example, as the information on the refractive index of water.

Figures 18, 19:
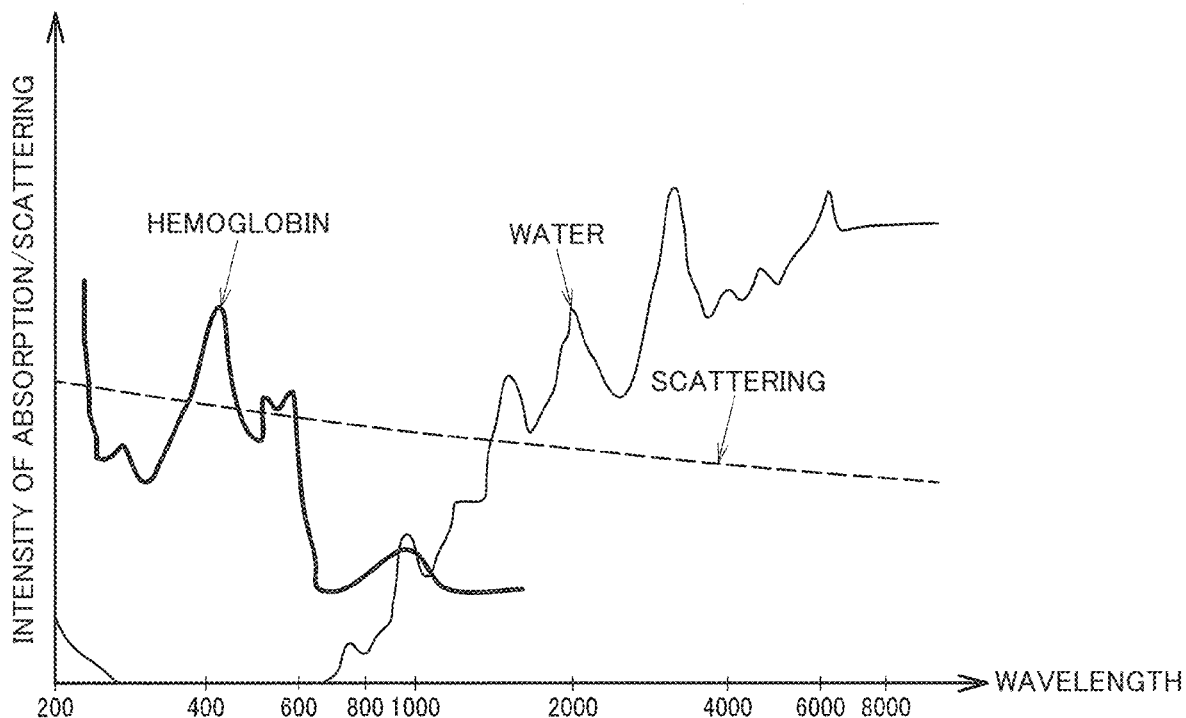
FIG. 18 illustrates an example of biological information.
FIG. 19 illustrates setting examples of light amount balance.

The water information database 132 further has biological information on the object to be observed. The biological information is information on the transmittance of hemoglobin contained in blood, for example. FIG. 18 illustrates an example of biological information. The information on the transmittance of hemoglobin includes a wavelength-absorption coefficient relationship, a wavelength-scattering coefficient relationship, or both, for example.

Figures 20, 21:
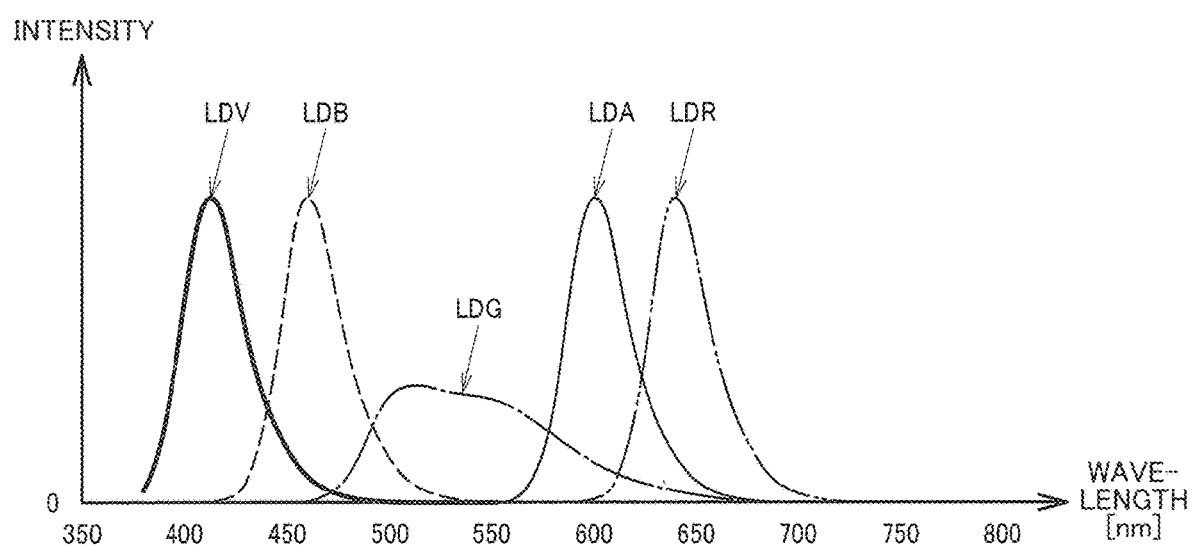
FIG. 20 illustrates setting examples of brightness correction coefficient.
FIG. 21 illustrates a first example of illumination light using five light sources including an amber light source.

FIGS. 19 and 20 are diagrams describing the operation of the second configuration example. FIG. 19 illustrates setting examples of light amount balance, and FIG. 20 illustrates setting examples of brightness correction coefficient.

In accordance with the underwater observation mode set by the observation mode switch button 420, the illumination mode switch control section 113 extracts the light amount balance and brightness correction value in the corresponding underwater illumination mode which are stored in the light source information database 131. The underwater observation mode has a plurality of settings in accordance with conditions for the water feed amount and blood-mixed water. In this example, the underwater observation modes include three modes of underwater observation 1 to underwater observation 3, but are not limited to them. The illumination mode switch control section 113 changes the color, brightness, or both of the illumination light in underwater observation, by changing the conditions for driving the light sources based on the extracted correction conditions. The illumination mode switch control section 113 may switch among underwater observations 1 to 3 by the time during which the water feed button is pressed, as a trigger for switching among the illumination conditions in the underwater illumination modes.

In FIGS. 19 and 20, the term "normal" refers to the normal observation mode that is not an underwater observation mode and in which to emit white illumination light. In FIG. 19, V1, V2, V3, and V4 indicate the light amount ratios of the light sources LDV, LDB, LDG, and LDR. In correspondence with the observation modes, the color temperatures of the illumination light are set and the light amount ratios for realizing the color temperatures are set. The coefficient in FIG. 20 are coefficients with which the light amount is to be multiplied, and are applied in common to all the light source emitting lights. That is, the total emission amount of the illumination light is controlled by the coefficients.

FIGS. 21 to 25 illustrate examples of illumination light using the five light sources including the amber light source. FIG. 21 illustrates spectral characteristics of lights emitted by the light sources. The light sources LDV, LDB, LDG, LDA, and LDR have peak wavelengths at or around 410 nm, 460 nm, 510 nm, 600 nm, and 640 nm, respectively. The light sources LDV, LDB, LDA, and LDR each have a half-value width of several tens of nm or the like, and the light source LDG has a half-value width of 100 nm or the like. In FIG. 21, the integrated value of spectra of the light sources is standardized to 1.

FIGS. 22 to 25 illustrate the spectra of the entire illumination light where the light sources emit light by the set light amounts.

Figure 22:
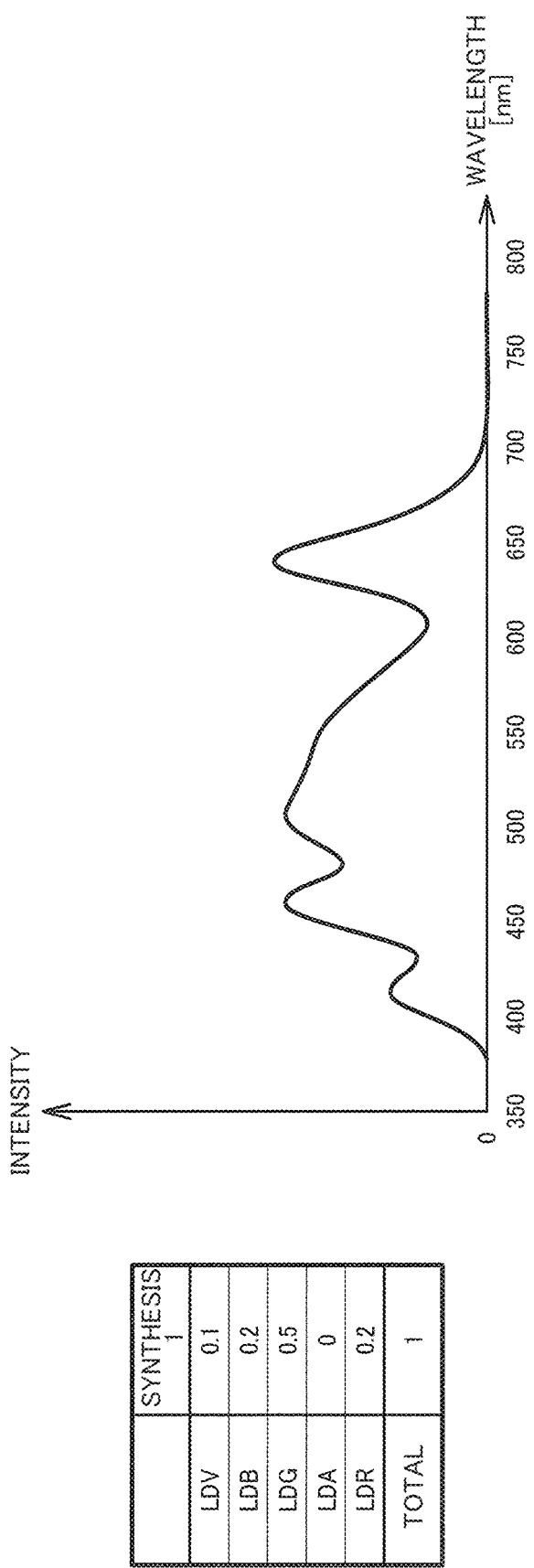
FIG. 22 illustrates a second example of illumination light using the five light sources including the amber light source.

FIG. 22 illustrates a first example of illumination light. The first example corresponds to white illumination light that is used in the normal observation mode. That is, the illumination light is set to a spectrum close to white by combining the light sources LDV, LDB, LDA, and LDR at a predetermined ratio. In the first example, the amber light source LDA is turned off.

Figure 23:
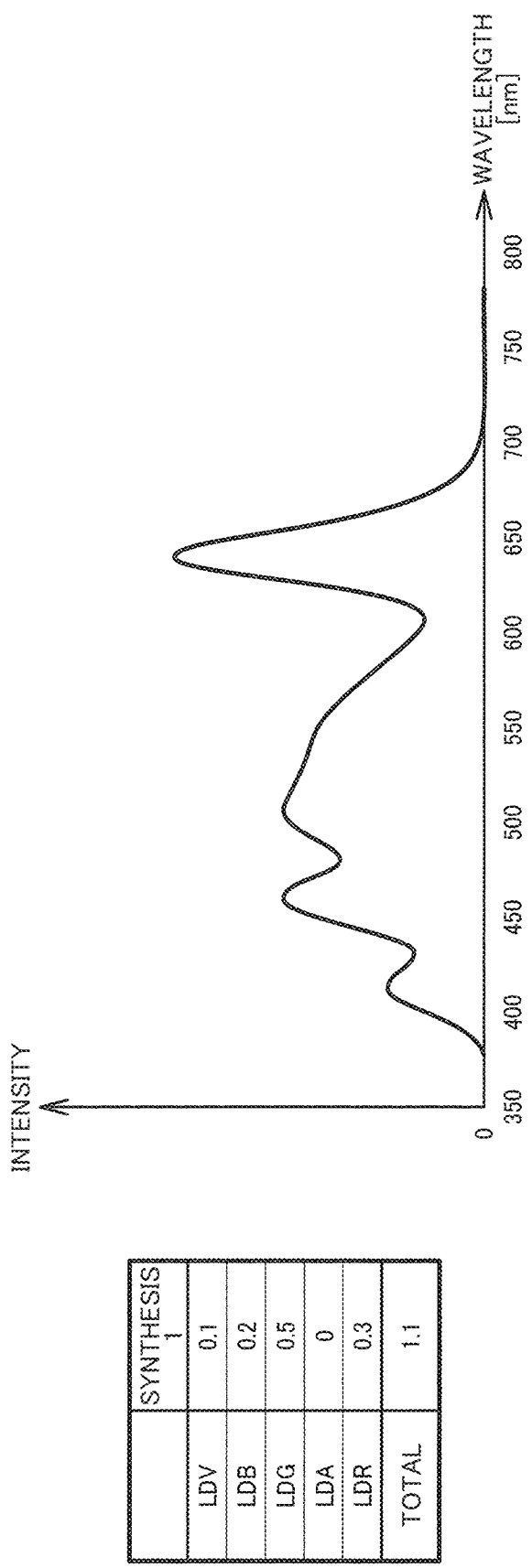
FIG. 23 illustrates a third example of illumination light using the five light sources including the amber light source.

FIG. 23 illustrates a second example of illumination light. The second example indicates illumination light that is used in the underwater observation mode and is selected in the case where the fluid is turbid in white. The ratio of the long wavelength components in the second example is increased to be higher than the ratio of the long wavelength components in the first example. The long wavelength components here refer to red light emitted by the light source LDR. In this illumination light, the long wavelength components are increased to take an anti-turbidity measure and maintain a spectrum close to white light. In the second example, the amber light source LDA is turned off.

Figure 24:
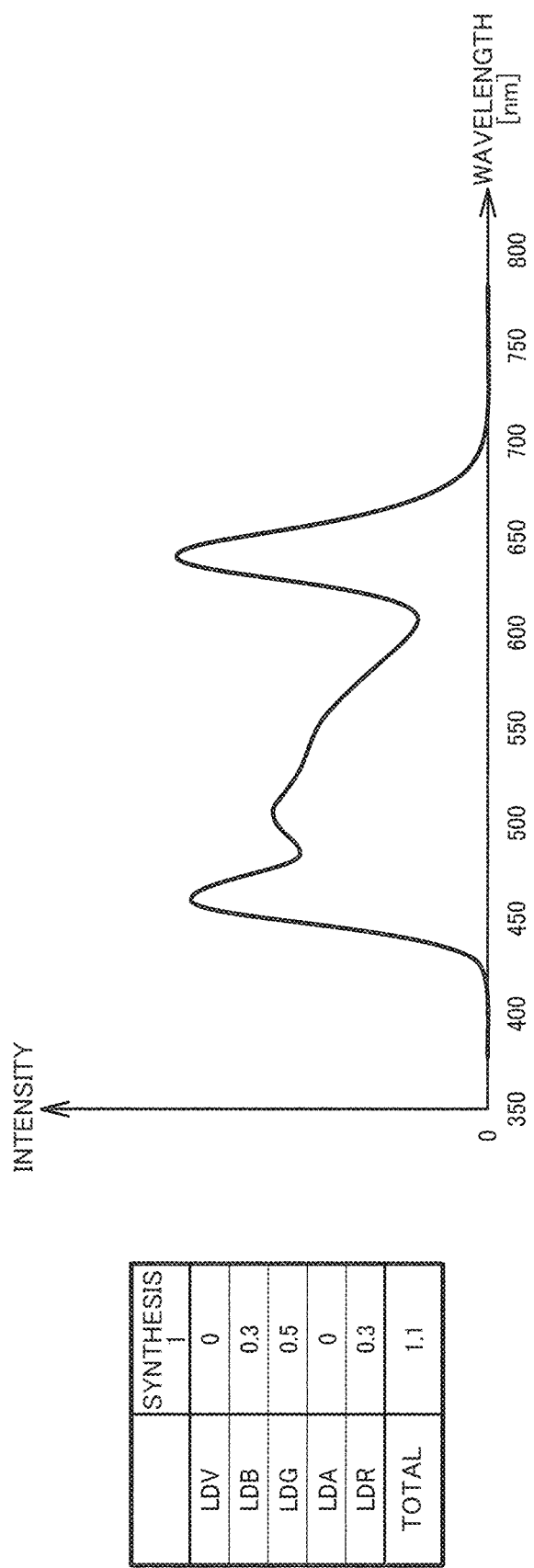
FIG. 24 illustrates a fourth example of illumination light using the five light sources including the amber light source.

FIG. 24 illustrates a third example of illumination light. The third example indicates illumination light that is used in the underwater observation mode and is selected in the case where the fluid is turbid due to blood. In the third example, the ratio of the light emission amount of the blue light source LDB to the light emission amount of the violet light source LDV is increased in comparison to that in the first example. In this example, the violet light source LDV is turned off and the light amount ratio of the blue light source LDB is increased to be larger than that in the first example. In this illumination light, the ratio of the light emission amount of the blue light source LDB to the light emission amount of the violet light source LDV is increased to take a measure against turbidity due to blood and maintain a spectrum close to white light. In the third example, the amber light source LDA is turned off.

Figure 25:
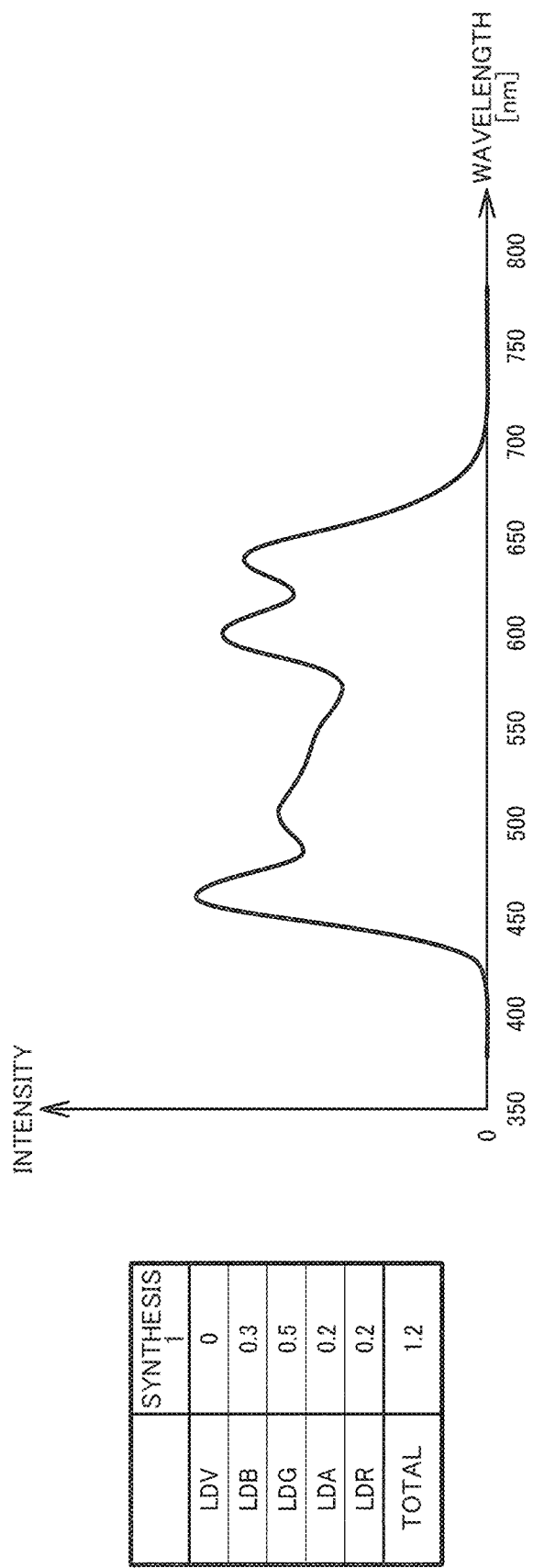
FIG. 25 illustrates a fifth example of illumination light using the five light sources including the amber light source.

FIG. 25 illustrates a fourth example of illumination light. The fourth example indicates illumination light that is used in the underwater observation mode and is selected to make a bleeding point easy to observe. In the fourth example, the light emission of the amber light source LDA is added to the third example. In addition, the light amount ratio of the red light source LDR is the same as that in the first example with the normal light. In this illumination light, the amber light with a peak wavelength at or around 600 nm is utilized to emphasize the unevenness of concentration of the blood and make it easy to observe a bleeding point.

According to the second configuration example described above, there is provided a table in which the amount of illumination light absorbed or reflected is considered, based on the absorption, scattering, and refractive index included in physical property information of water fed from the water feed device 150 and the absorption, scattering, and refractive index included in the physical property information of hemoglobin and blood. This table is a table for correcting the balance of the illumination light amount and the brightness of the illumination light. With this table, it is possible to set the illumination light suited for the corresponding underwater observation mode. Accordingly, observation can be performed under proper illumination light conditions in the normal observation and the underwater observation. In addition, the control of the illumination light is implemented by the plurality of light sources to realize finer color and brightness adjustments.

5. Third Configuration Example

A third configuration example using AI processing in a processing section 120 and an illumination mode switch control section 113 will be described. A configuration of an endoscope system 10 is similar to that in the second configuration example illustrated in FIG. 17. In the third configuration example, the observation mode switch button 420 may be omitted. Constituent elements already described in relation to the first or second configuration example are given identical reference signs and description thereof will be omitted as appropriate.

In the third configuration example, the processing section 120 detects, by AI processing, the degree of water seen in the captured image, the degree of white turbidity of the water, and the amount of blood contained in the water. The AI processing here refers to an inference process using a trained model obtained by machine learning. Specifically, the processing section 120 identifies the observation state by the AI processing based on a captured image and a water information database 132. The observation state refers to an underwater observation in which the leading end of a scope 200 and an object 1 are under water or a through-water observation in which the leading end of the scope 200 is not under water but the object 1 is under water. The processing section 120 also identifies the state water in the captured image by the AI processing based on the captured image and the water information database 132. The water state indicates the boundary between a region in the presence of water and a region in the absence of water, the region in the presence of water, the color density of the image of the region in the presence of water, or a combination thereof, for example.

The illumination mode switch control section 113 corrects the light amount ratio of the light sources by the AI processing, in accordance with the observation state and the water state identified by the processing section 120. Specifically, the observation state and the water state are machine-learned from the normal observation image, and a trained model obtained by the machine learning is stored in a storage section 130 of the endoscope system 10. The illumination mode switch control section 113 corrects the illumination conditions by an inference process using the trained model to optimize the illumination conditions. In the image recognition process and AI processing, the corrected light amounts may be updated or controlled in accordance with temporal changes in the observation state or the water state in the image.

Figure 26:
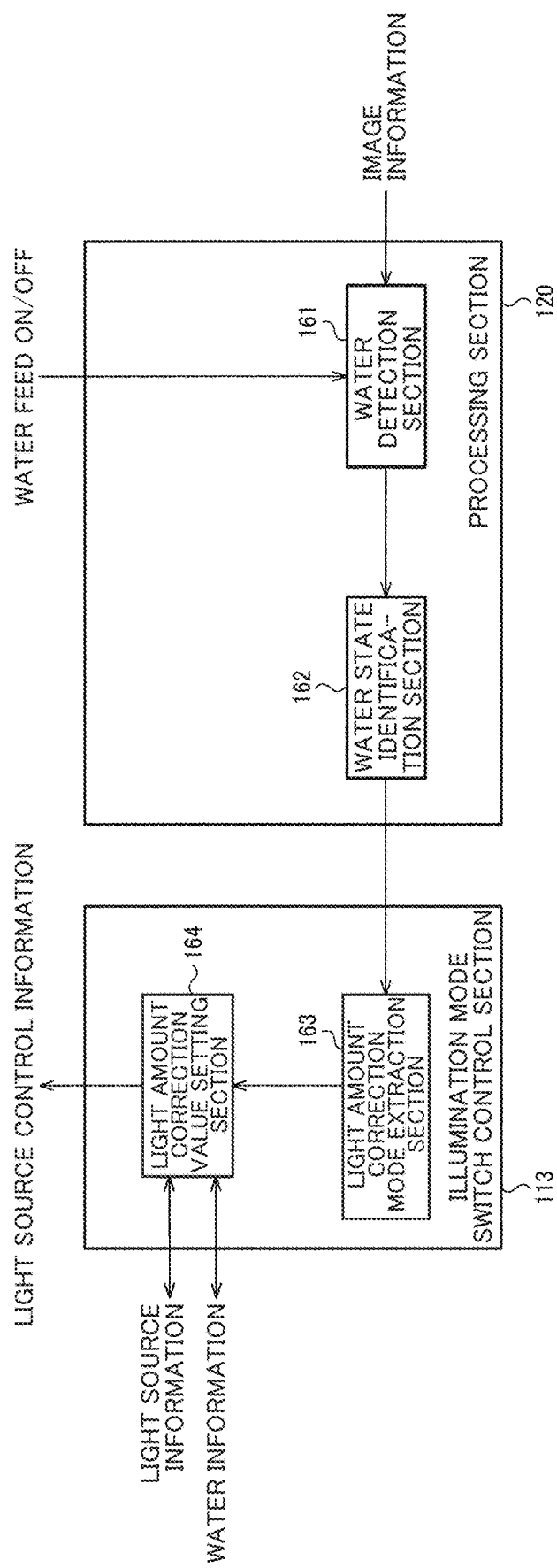
FIG. 26 illustrates a detailed configuration example of a processing section and an illumination mode switch control section in a third configuration example.

FIG. 26 illustrates a detailed configuration example of the processing section 120 and the illumination mode switch control section 113 in the third configuration example. The processing section 120 includes a water detection section 161 and a water state identification section 162. The illumination mode switch control section 113 includes a light amount correction mode extraction section 163 and a light amount correction value setting section 164. The water state identification section 162, the light amount correction mode extraction section 163, and the light amount correction value setting section 164 perform the AI processing.

Figure 27:
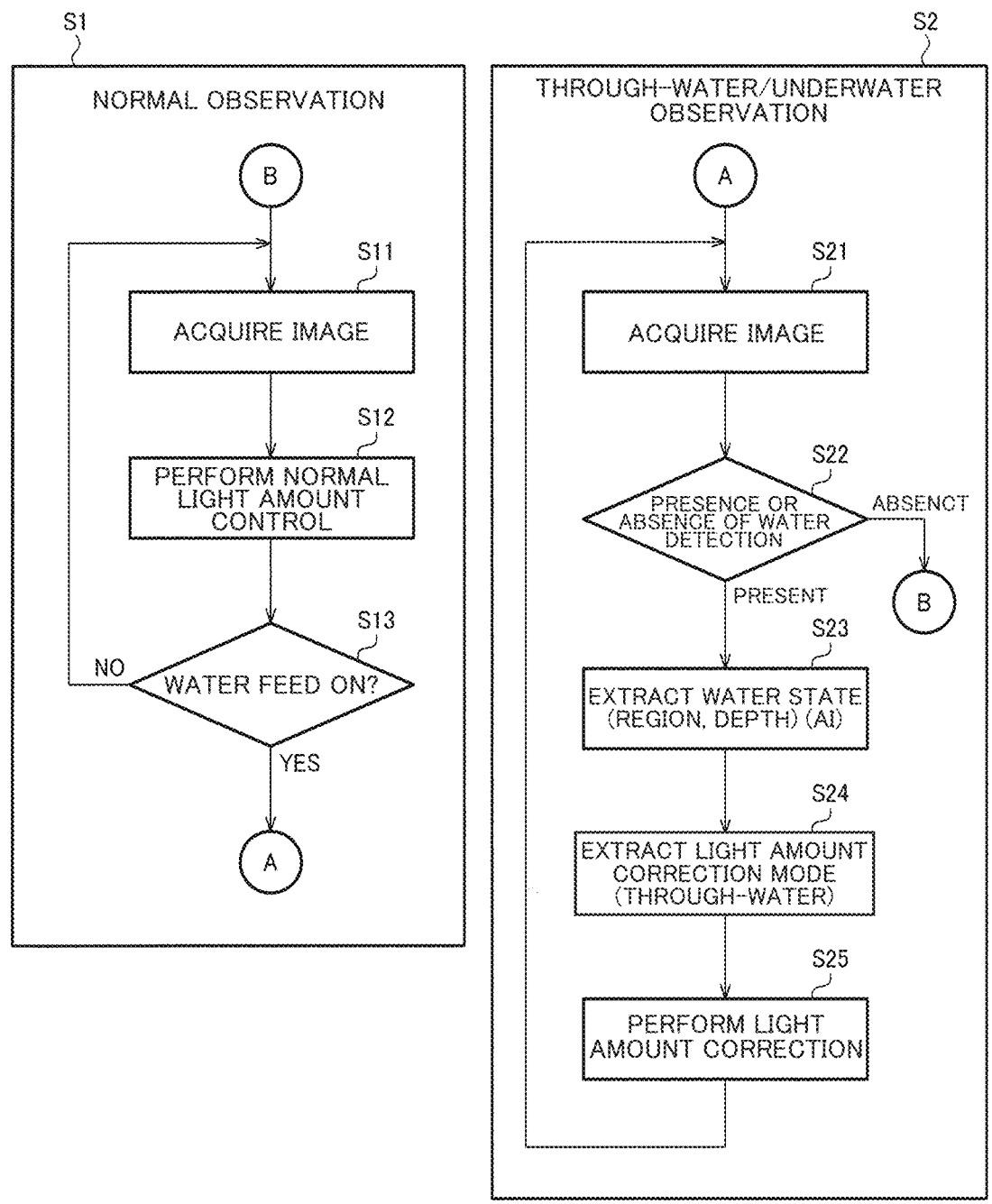
FIG. 27 illustrates a flowchart of processing in the third configuration example.

FIG. 27 is a process flowchart in the third configuration example. The flow in the normal observation indicated with S1 will be described first. In step S11, an imaging section 230 captures an image of the object 1, and the processing section 120 generates a captured image. In step S12, a system control section 112 and the light source control section 111 perform a normal light amount control based on the brightness of the captured image. The normal light amount control is a light adjustment control for maintaining the brightness of the captured image at a constant level. In step S13, the system control section 112 inputs a water feed ON/OFF signal indicating whether water feed is on or off to the water detection section 161. Based on the water feed ON/OFF signal, the water detection section 161 determines whether the water feed from a water feed device 150 to the object 1 is on. If the water detection section 161 determines that the water feed is off, steps S11 to S13 are repeated.

If the water detection section 161 determines that the water feed is on, the flow of through-water or underwater observation indicated with S2 is executed. In step S21, the imaging section 230 captures an image of the object 1, and the processing section 120 generates a captured image. In step S22, based on the water feed ON/OFF signal, the water detection section 161 determines whether the water feed from the water feed device 150 to the object 1 is on. If the water detection section 161 determines that the water feed is off, the flow of normal observation indicated with S1 is executed. If the water detection section 161 determines that the water feed is on, in step S23, the water state identification section 162 extracts the water state by the AI processing. The water state indicates the boundary between a region in the presence of water and a region in the absence of water, the region in the presence of water, the color density of the image of the region in the presence of water, or a combination thereof, for example. In step S24, from the water state extracted by the AI processing, the light amount increase/decrease correction values of the light sources are extracted based on the information in the light source information database 131 and the water information database 132. The light amount increase/decrease correction values are correction values for acquiring an image with the same color tone and brightness as those of the normal light, or correction values in accordance with the blood amount as in the illumination light using amber light, for example. In step S24, the light amount correction value setting section 164 outputs light source control information based on the light amount increase/decrease correction values to the system control section 112, and the system control section 112 and the light source control section 111 execute the light amount corrections of the light sources based on the light source control information.

According to the third configuration example, AI processing is executed based on the transparency, blood-mixture, or white turbidity that are included in the information of the water region obtained by image recognition. By this AI processing, the correction values of the illumination light considering absorption, scattering, and reflection included in the optical characteristic information of water are extracted. Since the illumination light is changed by the correction values, it is possible to provide an image easy to observe under less influence of the water. In addition, even if the state of the water temporally changes, the AI processing makes it possible to set the illumination mode suited for underwater observation conditions while setting proper color and brightness of the illumination light, with the use of water information and learning data by image recognition.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:
1. An endoscope system comprising:
a light source that emits illumination light;
an image sensor that captures an image of an object toward which the illumination light is emitted; and
a processor,
the processor being configured to perform:
determining whether a fluid is present in the object;
in a case where the fluid is not present in the object, switching to a first observation mode in which to illuminate the object by first illumination light; and
in a case where the fluid is present in the object, switching to a second observation mode in which to illuminate the object by second illumination light, wherein
the second illumination light is larger than the first illumination light in a relative ratio of long wavelength components wherein the object is a biological body, and the processor controls the light source such that as the fluid contains a larger amount of body fluid or more tissue fragments, a relative ratio of the long wavelength components in the spectrum of illumination light becomes higher.
2. The endoscope system as defined in claim 1, wherein the processor
controls switching among a plurality of observation modes including two or more of
the first observation mode to be selected in a case where the fluid is not present,
the second observation mode to be selected in a case where the degree of transparency of the fluid is relatively high, and
the third observation mode to be selected in a case where the degree of transparency of the fluid is relatively low, and
performs at least one control of
a control of switching, in accordance with switching between the first observation mode and the second observation mode, the illumination light between the first illumination light relating to the first observation mode and the second illumination light relating to the second observation mode,
a control of switching, in accordance with switching between the second observation mode and the third observation mode, the illumination light between the second illumination light relating to the second observation mode and third illumination light relating to the third observation mode and,
a control of switching, in accordance with switching between the first observation mode and the third observation mode, the illumination light between the first illumination light relating to the first observation mode and the third illumination light relating to the third observation mode.

3. The endoscope system as defined in claim 2, wherein the third illumination light is larger than the second illumination light in a relative ratio of long wavelength components in the spectrum.

4. The endoscope system as defined in claim 3, wherein
the second illumination light and the third illumination light are illumination lights obtained by increasing the long wavelength components of normal light, and
a degree of increase in the long wavelength components in the third illumination light is greater than a degree of increase in the long wavelength components in the second illumination light.

5. The endoscope system as defined in claim 3, wherein the second illumination light is illumination light obtained by increasing the long wavelength components of normal light, and
the third illumination light is special light that includes narrow band light corresponding to the long wavelength components.

6. The endoscope system as defined in claim 2, wherein
the object is a biological body,
the fluid contains blood, and
at least one of the second illumination light and the third illumination light includes light in a wavelength region of amber.

7. The endoscope system as defined in claim 2, wherein
the object is a biological body,
the fluid contains blood, and
a ratio of blue components to violet components in the spectrum of at least one of the second illumination light or the third illumination light is higher than a ratio of the blue components to the violet components in the spectrum of normal light.

8. The endoscope system as defined in claim 2, wherein
the processor performs a process based on the captured image captured by the image sensor,
the third illumination light includes light in a wavelength region of amber, and
the processor performs a process of detecting a bleeding point in the object, based on the captured image captured when the object is irradiated with the third illumination light, and performs a process of displaying the detected bleeding point.

9. The endoscope system as defined in claim 1, comprising a water feed outlet that supplies the fluid to the object, wherein
the processor controls the light source such that as a larger amount of the fluid is supplied by the water feed outlet, a relative ratio of the long wavelength components in the spectrum of the illumination light becomes higher.

10. The endoscope system as defined in claim 1, wherein
in a case where the degree of transparency of the fluid is equal to or higher than a predetermined threshold, the processor controls the light source such that a difference between the image captured by the image sensor and a reference image captured in the absence of the fluid is equal to or smaller than a predetermined value.

11. The endoscope system as defined in claim 10, wherein
in a case where the degree of transparency of the fluid is lower than the predetermined threshold, the processor controls the light source such that a difference between the image captured by the image sensor and a second reference image different from the reference image is equal to or smaller than a predetermined value.

12. The endoscope system as defined in claim 1, wherein
the processor performs a process based on the captured image captured by the image sensor, and
in a case where the processor controls the light source such that a relative ratio of the long wavelength components in the spectrum of the illumination light becomes large, the processor performs image processing on the captured image so as to reduce contribution of the long wavelength components.

13. The endoscope system as defined in claim 1, wherein
the processor performs a process based on the captured image captured by the image sensor, and
the processor performs a structure enhancement process on the captured image such that contrast of a region of interest becomes equal to or greater than a predetermined threshold.

14. The endoscope system as defined in claim 1, wherein
the processor performs a process based on a trained model that is acquired by machine learning of a relationship between a learning image and information related to the fluid or a relationship between the learning image and information related to recommended illumination light, and
the processor determines a control parameter for controlling the spectrum of the illumination light based on the captured image captured by the image sensor and the trained model, and controls the light source based on the determined control parameter.

15. The endoscope system as defined in claim 14, wherein the trained model is a model that is acquired by machine learning of a relationship among the learning image, information on the illumination light used in capturing the learning image, and information related to the liquid, or is a model that is acquired by machine learning of a relationship among the learning image, the information on the illumination light used in capturing the learning image, and the information related to the recommended illumination light.

16. The endoscope system as defined in claim 1, wherein
the processor performs a process based on a trained model that is acquired by machine learning of a relationship between a learning image and a bleeding point in the object, and
the processor detects the bleeding point based on the captured image captured by the image sensor and the trained model.

17. The endoscope system as defined in claim 16, wherein
the trained model is a model that is acquired by machine learning of a relationship among the learning image, information related to the fluid, and the bleeding point, or is a model that is acquired by machine learning of a relationship among the learning image, information on the illumination light used in capturing the learning image, and the bleeding point.

18. A control device comprising a processor,
the processor being configured to perform:
determining whether a fluid is present in the object;
in a case where the fluid is not present in the object, switching to a first observation mode in which to illuminate the object by first illumination light; and in a case where the fluid is present in the object, switching to a second observation mode in which to illuminate the object by second illumination light, wherein the second illumination light is larger than the first illumination light in a relative ratio of long wavelength components wherein the object is a biological body, and the processor controls the light source such that as the fluid contains a larger amount of body fluid or more tissue fragments, a relative ratio of the long wavelength components in the spectrum of illumination light becomes higher.

19. A control method of a control device, comprising:

determining whether a fluid is present in the object;

in a case where the fluid is not present in the object, switching to a first observation mode in which to illuminate the object by first illumination light; and in a case where the fluid is present in the object, switching to a second observation mode in which to illuminate the object by second illumination light, wherein the second illumination light is larger than the first illumination light in a relative ratio of long wavelength components wherein the object is a biological body, and the processor controls the light source such that as the fluid contains a larger amount of body fluid or more tissue fragments, a relative ratio of the long wavelength components in the spectrum of illumination light becomes higher.

* * * * *